United States Patent
Goldman

(10) Patent No.: US 8,251,948 B2
(45) Date of Patent: Aug. 28, 2012

(54) MULTI-FUNCTION CATHETER AND USE THEREOF

(75) Inventor: Robert J. Goldman, San Jose, CA (US)

(73) Assignee: Vascular Designs, Inc., San Jose, CA (US)

( * ) Notice: Subject to any disclaimer, the term of this patent is extended or adjusted under 35 U.S.C. 154(b) by 0 days.

(21) Appl. No.: 12/405,592

(22) Filed: Mar. 17, 2009

(65) Prior Publication Data

US 2009/0182227 A1    Jul. 16, 2009

Related U.S. Application Data

(60) Division of application No. 11/971,859, filed on Jan. 9, 2008, now Pat. No. 8,062,251, which is a continuation-in-part of application No. 11/097,582, filed on Apr. 1, 2005, which is a continuation-in-part of application No. 10/355,017, filed on Jan. 31, 2003, now Pat. No. 7,645,259.

(60) Provisional application No. 60/353,305, filed on Feb. 1, 2002, provisional application No. 60/387,260, filed on Jun. 7, 2002.

(51) Int. Cl.
*A61M 29/00* (2006.01)

(52) U.S. Cl. ........... 604/96.01; 604/101.01; 604/101.03; 604/101.05

(58) Field of Classification Search ... 604/96.01–103.14
See application file for complete search history.

(56) References Cited

U.S. PATENT DOCUMENTS

| | | | |
|---|---|---|---|
| 4,573,966 A * | 3/1986 | Weikl et al. | 604/509 |
| 4,610,662 A * | 9/1986 | Weikl et al. | 604/509 |
| 4,636,195 A | 1/1987 | Wolinsky | |
| 4,655,746 A | 4/1987 | Daniels et al. | |
| 4,696,668 A * | 9/1987 | Wilcox | 604/28 |
| 4,708,718 A | 11/1987 | Daniels | |
| 4,714,460 A * | 12/1987 | Calderon | 604/28 |

(Continued)

FOREIGN PATENT DOCUMENTS

EP    0920882    9/1991

(Continued)

OTHER PUBLICATIONS

PCT/US2009/030434 International Search Report, dated Feb. 26, 2009.

(Continued)

*Primary Examiner* — Nicholas Lucchesi
*Assistant Examiner* — Gerald Landry, II
(74) *Attorney, Agent, or Firm* — Morrison & Foerster LLP

(57) ABSTRACT

A catheter for delivering an agent to an area of treatment is presented. The catheter includes a catheter body, a balloon assembly coupled to the catheter body, a first lumen, and a second lumen. The balloon assembly has spaced-apart balloons that define an area between the balloons. The first lumen extends along the catheter body to pass an inflation material to the balloons to control an inflation level of the balloons. The second lumen extends along the catheter body and having an outlet in the area between the balloons. There may be a third lumen for bypassing a biological fluid such as blood while the catheter is being used. The method of using this catheter is also presented. The method entails simultaneously inflating the balloons to isolate a treatment area and adding an agent to the treatment area through one of the lumens.

13 Claims, 19 Drawing Sheets

U.S. PATENT DOCUMENTS

| | | | |
|---|---|---|---|
| 4,824,436 A * | 4/1989 | Wolinsky | 604/509 |
| 4,832,688 A * | 5/1989 | Sagae et al. | 604/509 |
| 5,090,960 A | 2/1992 | Don Michael | |
| 5,160,321 A | 11/1992 | Sahota | |
| 5,163,905 A | 11/1992 | Don Michael | |
| 5,176,638 A | 1/1993 | Don Michael | |
| 5,222,941 A | 6/1993 | Don Michael | |
| 5,257,634 A | 11/1993 | Kroll | |
| 5,265,623 A | 11/1993 | Kroll et al. | |
| 5,330,509 A | 7/1994 | Kroll et al. | |
| 5,409,495 A | 4/1995 | Osborn | |
| 5,415,636 A * | 5/1995 | Forman | 604/101.03 |
| 5,423,744 A | 6/1995 | Gencheff et al. | |
| 5,439,446 A | 8/1995 | Barry | |
| 5,454,839 A | 10/1995 | Anderson et al. | |
| 5,460,610 A | 10/1995 | Don Michael | |
| 5,462,529 A | 10/1995 | Simpson et al. | |
| 5,470,313 A | 11/1995 | Crocker et al. | |
| 5,514,092 A * | 5/1996 | Forman et al. | 604/101.03 |
| 5,516,336 A | 5/1996 | McInnes et al. | |
| 5,554,119 A | 9/1996 | Harrison et al. | |
| 5,558,642 A | 9/1996 | Schweich, Jr. et al. | |
| 5,569,197 A | 10/1996 | Helmus et al. | |
| 5,628,730 A | 5/1997 | Shapland et al. | |
| 5,649,974 A | 7/1997 | Nelson et al. | |
| 5,662,609 A | 9/1997 | Slepian | |
| 5,674,198 A | 10/1997 | Leone | |
| 5,713,944 A | 2/1998 | Kroll | |
| 5,792,106 A | 8/1998 | Mische | |
| 5,868,719 A | 2/1999 | Tsukernik | |
| 5,899,917 A | 5/1999 | Edwards et al. | |
| 5,925,066 A | 7/1999 | Kroll et al. | |
| 6,015,414 A | 1/2000 | Werp et al. | |
| 6,022,336 A | 2/2000 | Zadno-Azizi et al. | |
| 6,027,510 A | 2/2000 | Alt | |
| 6,039,757 A | 3/2000 | Edwards et al. | |
| 6,056,721 A | 5/2000 | Shulze | |
| 6,132,426 A | 10/2000 | Kroll | |
| 6,136,011 A | 10/2000 | Stambaugh | |
| 6,139,517 A | 10/2000 | Macoviak et al. | |
| 6,171,296 B1 | 1/2001 | Chow | |
| 6,214,022 B1 | 4/2001 | Taylor et al. | |
| 6,231,562 B1 | 5/2001 | Khosravi et al. | |
| 6,231,588 B1 | 5/2001 | Zadno-Azizi | |
| 6,254,563 B1 | 7/2001 | Macoviak et al. | |
| 6,287,306 B1 | 9/2001 | Kroll et al. | |
| 6,287,320 B1 * | 9/2001 | Slepian | 606/194 |
| 6,290,485 B1 | 9/2001 | Wang | |
| 6,290,673 B1 | 9/2001 | Shanley | |
| 6,290,689 B1 | 9/2001 | Delaney et al. | |
| 6,291,582 B1 | 9/2001 | Dordick et al. | |
| 6,299,597 B1 * | 10/2001 | Buscemi et al. | 604/101.03 |
| 6,299,599 B1 * | 10/2001 | Pham et al. | 604/113 |
| 6,344,041 B1 | 2/2002 | Kupiecki et al. | |
| 6,366,808 B1 | 4/2002 | Schroeppel et al. | |
| 6,409,716 B1 | 6/2002 | Sahatjian et al. | |
| 6,428,558 B1 | 8/2002 | Jones et al. | |
| 6,438,426 B2 | 8/2002 | Hofstad et al. | |
| 6,582,448 B1 | 6/2003 | Boyle et al. | |
| 6,679,879 B2 | 1/2004 | Shadduck | |
| 6,695,864 B2 | 2/2004 | Macoviak et al. | |
| 6,738,663 B2 | 5/2004 | Schroeppel et al. | |
| 6,780,181 B2 | 8/2004 | Kroll et al. | |
| 6,835,189 B2 | 12/2004 | Musbach et al. | |
| 7,144,407 B1 | 12/2006 | Lasersohn | |
| 7,412,285 B2 | 8/2008 | Schroeppel et al. | |
| 7,481,800 B2 * | 1/2009 | Jacques | 604/264 |
| 7,645,259 B2 | 1/2010 | Goldman | |
| 7,742,811 B2 | 6/2010 | Schroeppel et al. | |
| 2001/0036451 A1 | 11/2001 | Goupil et al. | |
| 2001/0041862 A1 * | 11/2001 | Glickman | 604/101.01 |
| 2003/0036726 A1 | 2/2003 | Forman et al. | |
| 2003/0114878 A1 * | 6/2003 | Diederich et al. | 606/192 |
| 2005/0267407 A1 | 12/2005 | Goldman | |
| 2007/0137651 A1 * | 6/2007 | Glassenberg et al. | 128/207.15 |
| 2008/0208118 A1 | 8/2008 | Goldman | |
| 2009/0182227 A1 | 7/2009 | Goldman | |
| 2010/0114021 A1 | 5/2010 | Goldman | |

FOREIGN PATENT DOCUMENTS

| | | | |
|---|---|---|---|
| JP | 8-52219 A | | 11/1995 |
| JP | 11-178929 A | | 7/1999 |
| JP | 2000-513625 A | | 10/2000 |
| JP | 2002-102354 A | | 4/2002 |
| WO | WO97 24154 | | 10/1997 |
| WO | WO 97/24154 | | 10/1997 |
| WO | WO-98/48884 A2 | | 11/1998 |
| WO | WO-98/48884 A3 | | 11/1998 |
| WO | WO-03/065872 A2 | | 8/2003 |
| WO | WO-03/065872 A3 | | 8/2003 |

OTHER PUBLICATIONS

PCT/US2009/030434 Written Opinion, dated Feb. 26, 2009.

International Search Report mailed Oct. 30, 2003, for PCT Application No. PCT/US03/02755, filed Jan. 31, 2003, one page.

Supplemental Partial European Search Report mailed Jul. 24, 2006, for EP Patent Application No. 03710793.5, filed Jan. 31, 2003, four pages.

Cliffton, E.E. et al. (Apr. 1963). "Technique for Visualization and Perfusion of Bronchial Arteries: Suggested Clinical and Diagnostic Applications," *Cancer* 16(4):444-452.

Cliffton, E.E. (May 1969). "Bronchial Artery Perfusion for Treatment of Advanced Lung Cancer," *Cancer* 23(5):1151-1157.

Esler, M.D. et al. (Dec. 4, 2010, e-pub. Nov. 17, 2010). "Renal Sympathetic Denervation in Patients with Treatment-Resistant Hypertension (The Symplicity HTN-2 Trial): A Randomised Controlled Trial," *Lancet* 376(9756):1903-1909.

Final Office Action mailed on Aug. 18, 2010, for U.S. Appl. No. 11/097,582, filed Apr. 1, 2005, eight pages.

Final Office Action mailed on Jun. 24, 2010, for U.S. Appl. No. 11/971,859, filed Jan. 9, 2008, ten pages.

Non-Final Office Action mailed on Mar. 31, 2011, for U.S. Appl. No. 11/097,582, filed Apr. 1, 2005, six pages.

Non-Final Office Action mailed on Feb. 15, 2011, for U.S. Appl. No. 11/971,859, filed Jan. 9, 2008, seven pages.

Non-Final Office Action mailed on Jun. 14, 2010, for U.S. Appl. No. 12/685,533, filed Jan. 11, 2010, eight pages.

Non-Final Office Action mailed on Nov. 27, 2009, for U.S. Appl. No. 11/097,582, filed Apr. 1, 2005, eight pages.

Non-Final Office Action mailed on Nov. 23, 2009, for U.S. Appl. No. 11/971,859, filed Jan. 9, 2008, seven pages.

Non-Final Office Action mailed May 11, 2009, for U.S. Appl. No. 11/971,859, filed Jan. 9, 2008, nine pages.

Non-Final Office Action mailed on Jul. 11, 2008, for U.S. Appl. No. 10/355,017, filed Jan. 31, 2003, seven pages.

Non-Final Office Action mailed on Jul. 30, 2007, for U.S. Appl. No. 10/355,017, filed Jan. 31, 2003, six pages.

Non-Final Office Action mailed on Oct. 11, 2006, for U.S. Appl. No. 10/355,017, filed Jan. 31, 2003, six pages.

Non-Final Office Action mailed on Feb. 23, 2005, for U.S. Appl. No. 10/355,017, filed Jan. 31, 2003, six pages.

Rousselot, L.M. et al. (Mar. 1, 1965). "Selective Concentration of Anticancer Drugs in the Liver: Hepatic-Artery Infusion and Induced Hepatic Outflow Block," *JAMA* 191(9):707-710.

* cited by examiner

300

302
PLACING THE MULTI-FUNCTION CATHETER AT THE PLAQUE SITE

304
INFLATING THE BALLOON ASSEMBLY TO CREATE A PERFUSION CHAMBER

306
DELIVERING A PLAQUE REMOVAL AGENT TO THE PERFUSION CHAMBER TO DISSOLVE THE PLAQUE

308
FORMING A STENT AT THE TREATMENT SITE

310
WITHDRAWING THE MULTI-FUNCTION CATHETER

```
                    ┌─────────────────────────────┐
                    │            902              │
                    │ PLACING THE CATHETER AT AN  │
                    │     AREA OF TREATMENT       │
                    └──────────────┬──────────────┘
                                   ▼
                    ┌─────────────────────────────┐
                    │            904              │
                    │  INFLATING THE BALLOON      │
                    │  ASSEMBLY TO CREATE A       │
                    │  SPACE BETWEEN BALLOONS     │
                    └──────────────┬──────────────┘
                                   ▼
                    ┌─────────────────────────────┐
                    │            906              │
                    │  DELIVERING AN AGENT TO     │
                    │  THE SPACE BETWEEN THE      │
                    │         BALLOONS            │
                    └──────────────┬──────────────┘
                                   ▼
                    ┌─────────────────────────────┐
                    │            908              │
                    │  DEFLATING THE BALLOON      │
                    │         ASSEMBLY            │
                    └──────────────┬──────────────┘
                                   ▼
                    ┌─────────────────────────────┐
                    │            910              │
                    │  WITHDRAWING THE CATHETER   │
                    │  FROM THE AREA OF TREATMENT │
                    └─────────────────────────────┘
```

FIG. 10

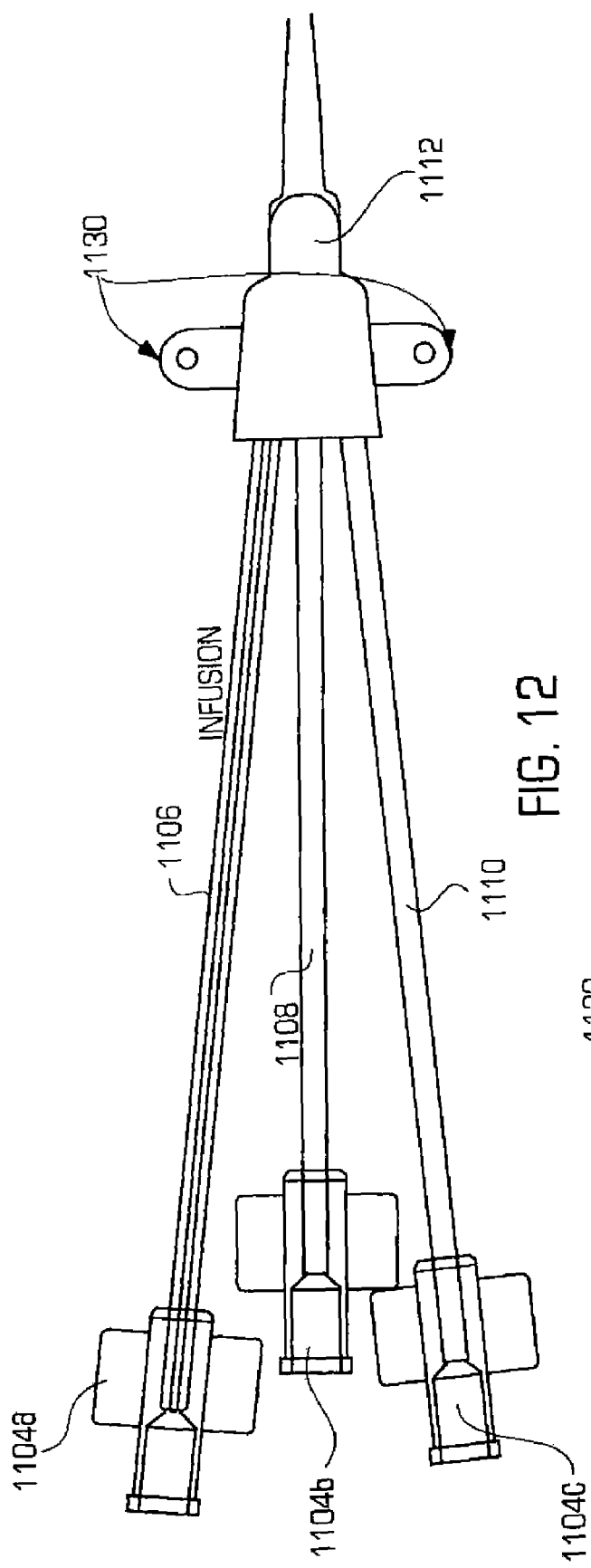
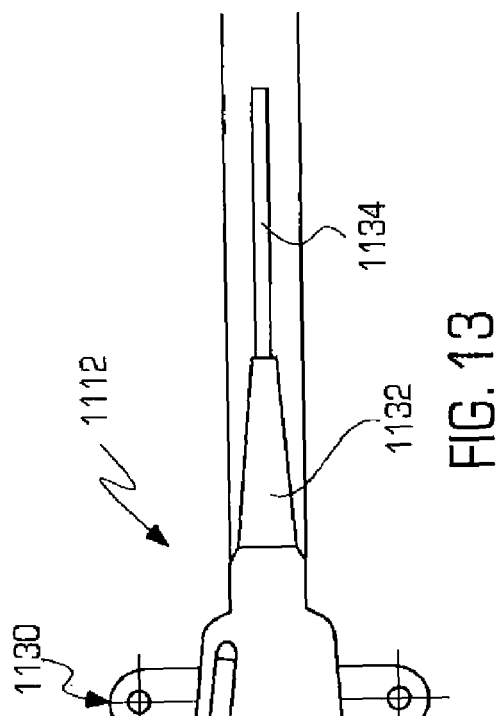
FIG. 12
FIG. 13

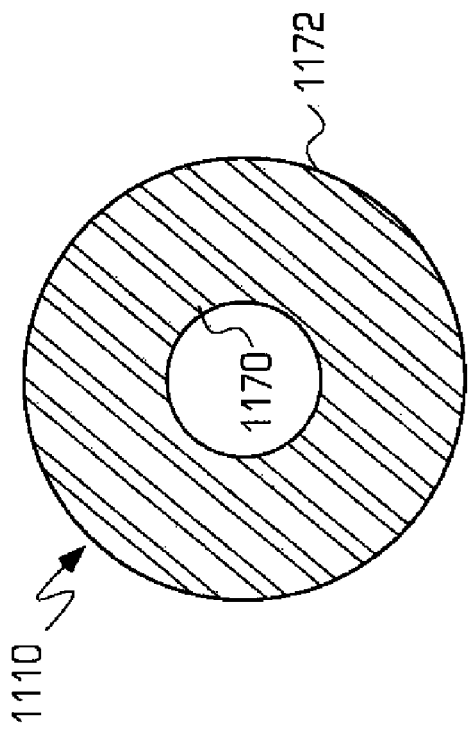
FIG. 17A
BALLOON
FIG. 17B
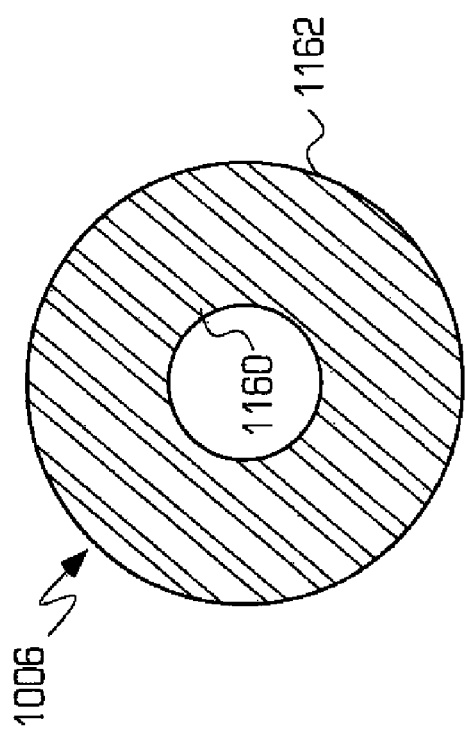
FIG. 16A
INFUSION
FIG. 16B

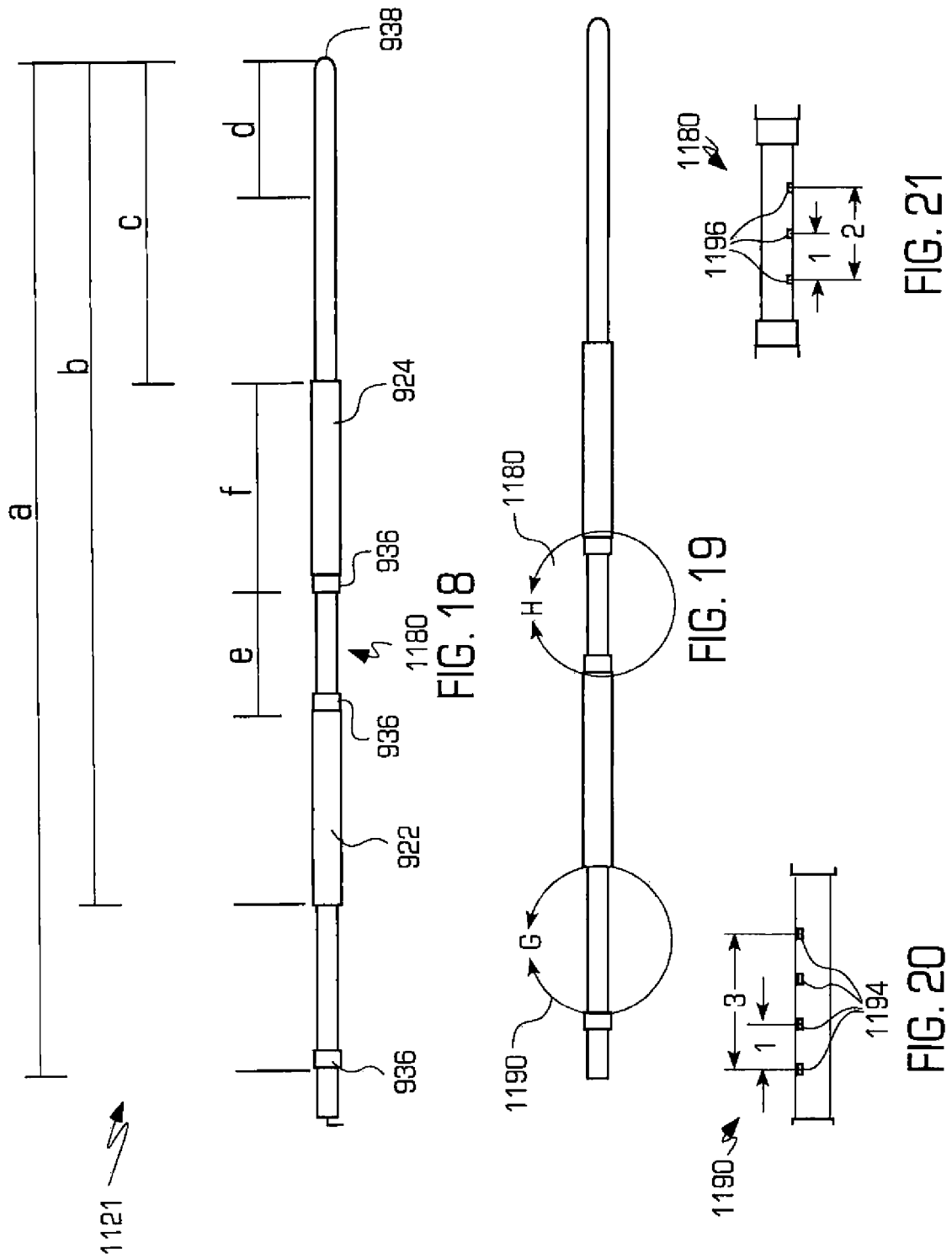

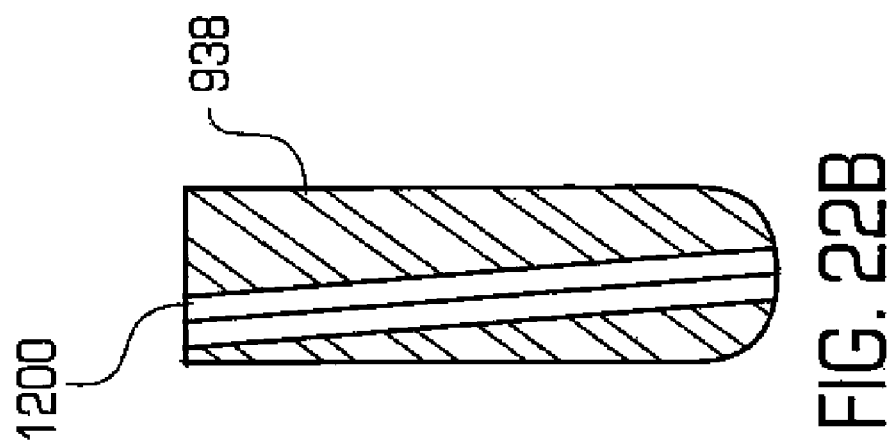
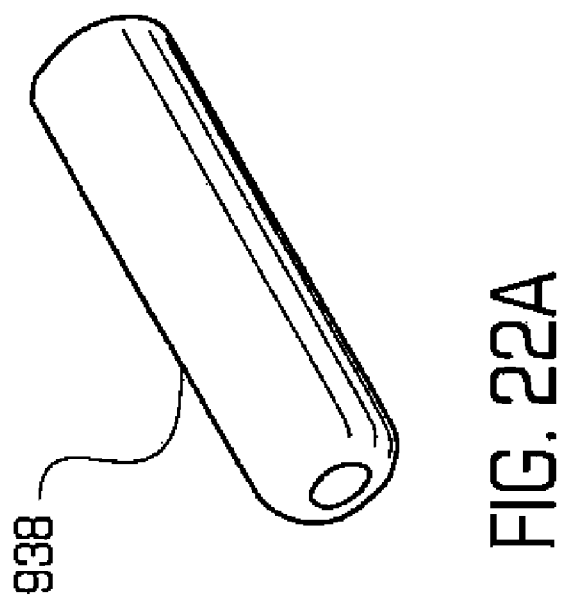

MULTI-FUNCTION CATHETER AND USE THEREOF

PRIORITY CLAIM

This application is a divisional of and claims priority under 35 USC 120 to U.S. patent application Ser. No. 11/971,859 filed on Jan. 9, 2008, entitled "Multi-Function Catheter and Use Thereof" which is a continuation in part of and claims priority under 35 USC 120 to U.S. patent application Ser. No. 11/097,582 filed on Apr. 1, 2005 and entitled "Multi-Function Catheter and Use Thereof" which is in turn a continuation-in-Part application of and claims priority under 35 USC 120 to U.S. Ser. No. 10/355,017 filed on Jan. 31, 2003, which in turn claims the benefit under 35 USC 119(e) to U.S. Provisional Application Nos. 60/353,305 filed on Feb. 1, 2002 and 60/387,260 filed on Jun. 7, 2002, all of which are incorporated by reference herein.

FIELD

Medical devices and procedures for medical treatment are described and, in particular, a catheter is described.

BACKGROUND

Catheters have been widely used to access the vascular system and other anatomical spaces in medical procedures. Catheters may be used for infusion of therapeutics and for the insertion or placement of substances or apparatuses for treating various disorders. Catheters may also be modified, for example, by the addition of balloon systems, for the treatment of arterial plaques and aneurisms.

Arterial plaques grow on arterial walls as cholesterol circulates in the blood, and as the plaques enlarge the arteries become narrow and stiffened. This process is called atherosclerosis, commonly known as "hardening of the arteries" because the plaque buildup thickens the walls of the arteries, narrowing the space through which blood flows. The narrowing or blockage of the vessel is also referred to as "stenosis."

One of the common methods for treating arterial plaques is balloon angioplasty. As an established procedure in the management of a variety of obstructive disorders of the vascular system, balloon angioplasty has been applied to obstructive lesions of the iliac, femoral, renal, coronary and cerebral vascular systems. Typically, a small flexible guide wire is advanced through a guiding catheter into the vessel and across the stenosis. A balloon catheter is then advanced over the wire and positioned across the stenosis. The balloon is usually inflated for a short period of time to dilate the vessel and is then deflated. Alternatively, stenosis may be treated by chemical means. For example, U.S. Pat. No. 4,636,195 to Harvey Wolinsky describes a catheter with distal and proximate balloon segments expandable to produce a chamber around an arterial plaque and a conduit for delivering a solubilizing liquid into the chamber to dissolve the plaque. U.S. Pat. No. 6,056,721 to John Shulze also describes a balloon catheter device for treating an obstructing material within a vascular conduit. The device comprises an elongate catheter body extending between a proximal end and a distal end. A balloon is attached at the distal end to block the flow of a body fluid and a drug is released from the catheter body to treat the obstructing material. Other methods for treating stenosis include ionizing radiation and laser evaporation.

All these procedures usually cause some degree of biological reaction of the vessel wall and often result in new growth and significant reduction of the vessel lumen (restenosis) at the treatment site. Therefore, it is a common procedure to place a stent at the treatment site after balloon angioplasty to prevent restenosis. The stent is usually introduced to the target area in a compressed form by an insertion catheter and then expanded in situ by means of a special balloon catheter. The stent will remain in position in its expanded state, supporting the wall of the vessel in a manner that essentially restores the original form of the vessel. The stent may also be formed in situ. For example, U.S. Pat. No. 6,039,757 to Stuart Edwards et al. generally describes a device for forming a fenestrated stent in situ in a body lumen. Briefly, the body lumen and the stent-forming device form a mold space within which a fluent composition is provided and transformed into a non-fluent composition in the shape of a stent with a series of fenestrations.

The term "aneurysm" refers to the abnormal enlargement or bulging of an artery caused by damage to or weakness in the blood vessel wall. Although aneurysms can occur in any type of the body's blood vessels, they almost always form in an artery. A ruptured aneurysm can lead to internal bleeding that often results in severe impairment of body functions and even death. Traditional treatment for aneurysms is surgical clipping which requires major surgery and cannot be performed on aneurysms inside vital organs, such as the brain. A much less-invasive technique, endovascular coiling, has been developed as a viable alternative to surgery for many patients whose aneurysms might otherwise go untreated. In an endovascular coiling procedure, a microcatheter is inserted into the femoral artery in a patient's groin area. The microcatheter is tracked through the patient's blood vessels (arteries), from the femoral artery up to the site of the aneurysm. Matrix coils are fed through the catheter and into the aneurysm, filling it and sealing it off from the artery. In animal studies, the coils were found to promote the development of connective (scar) tissue inside the aneurysm. The connective tissue excluded the aneurysm from arterial blood flow. An aneurysm occluded from blood circulation may have a decreased risk of rupture.

In order to treat an aneurysm effectively with an endovascular coil system, the coil must be inserted into the aneurysm and positioned inside the aneurysm in a proper configuration. The process, however, is often time-consuming and requires experienced operators.

Another illness that is currently not treated effectively is cancer. Most current efforts to eliminate tumors include systematic approaches such as chemotherapy, radiation, and surgical removal of tissues. When a tumor is vascular, chemotherapy and radiation treatments are less effective than desired because it is difficult to target the tumor with an effective level of specificity and only a small percentage of the chemotherapy and radiation get "pushed" into the capillaries that feed the tumor. With only a small percentage of the chemotherapy and radiation actually getting to the tumor, more of the chemotherapy and radiation end up reaching the healthy tissues instead of the tumor. A treatment method that allows a more targeted approach to kill the tumor is desirable.

Most catheters are specialized and can only be used for a specific medical procedure. For example, an angioplasty catheter cannot be used for treating aneurysms and, vice versa, catheters designed for treating aneurysms cannot be used for stenosis. In the case of balloon angioplasty, the angioplasty and stent installation typically require two different disposable, low profile guiding catheters. The insertion and removal of the catheters are time-consuming processes and the catheters are expensive.

In order to reduce costs and improve efficiency, it would be desirable to have one catheter that could be used to treat multiple illnesses such as stenosis, aneurysm, and vascular cancer.

BRIEF DESCRIPTION OF THE DRAWINGS

FIG. 10 is a flow diagram showing a method of treatment using the alternative catheter of FIG. 9;

FIG. 12 illustrates more details of a proximal portion of the multi-function catheter shown in FIG. 11;

FIG. 13 illustrates more details of the manifold that is part of the multi-function catheter shown in FIG. 11;

FIGS. 16A and 16B illustrates more details of an infusion extension that is part of the multi-function catheter shown in FIG. 11;

FIGS. 17A and 17B illustrates more details of a balloon extension that is part of the multi-function catheter shown in FIG. 11;

FIGS. 18-21 illustrate more details of a treatment portion of the multi-function catheter shown in FIG. 11; and FIGS. 22A and 22B illustrates more details of a distal tip portion of the multi-function catheter shown in FIG. 11.

DETAILED DESCRIPTION OF ONE OR MORE EMBODIMENTS

Figure 1A:
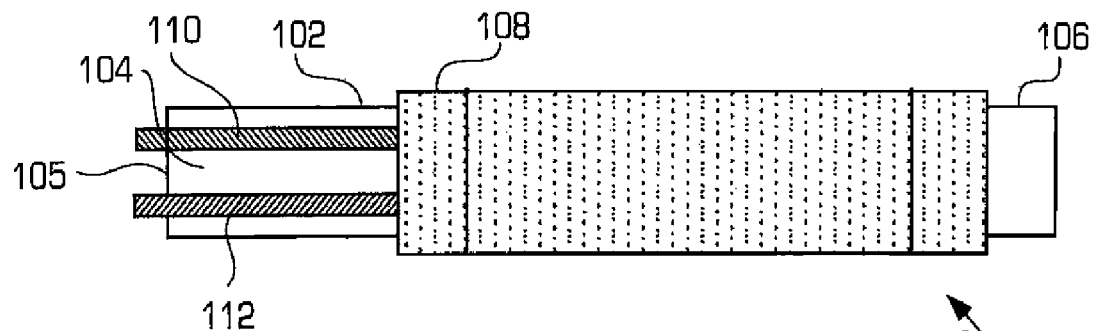
FIGS. 1A, 1B and 1C illustrate side views of various embodiments of a multi-function catheter with an uninflated balloon in accordance with the teachings of the present invention.

In one embodiment, a catheter is provided for delivering an agent to an area of treatment. The catheter includes a catheter body, a balloon assembly coupled to the catheter body, a first lumen, and a second lumen. The balloon assembly has spaced-apart balloons that define an area between the balloons. The first lumen extends along the catheter body to pass an inflation material to the balloons to control an inflation level of the balloons. The second lumen extends along the catheter body and having an outlet in the area between the balloons. The balloon assembly may have two balloon elements, although the number is balloon elements is not so limited. The second lumen may be used to deliver a treatment material/agent to a treatment site that is located between the two balloon elements wherein the treatment material is kept localized in the treatment site. The treatment material/agent may be a chemotherapy agent, an anti-tumor agent, a pre-stent agent, a saline material, an embolic material, an imaging agent, a plaque removal agent, an adhesive agent and/or a combination of one or more of these as described below in more detail. The treatment material/agent may be a liquid or gas or dissolved solid. In each of the embodiments described below, the catheter may be made of a hydrophilic material or have a hydrophilic coating that allows easier insertion of the catheter.

In another embodiment, a method of delivering an agent to a treatment area is described. The method includes providing a catheter that is attached to inflatable balloons and positioning the catheter so that the area of treatment is between the balloons. The catheter has a first lumen and a second lumen extending along the catheter. The inflation level of the balloons is simultaneously controlled to create the treatment area between the balloons. The inflation level is controlled by passing an inflation material, such as saline, through the first lumen that has an opening into each of the balloons. The agent is passed into the treatment area through a second lumen. This method may be used with two inflatable balloons, although the method is not so limited.

In yet another embodiment, a catheter for cancer treatment is provided. The catheter includes a catheter body having a proximal end and a distal end, a first balloon positioned to inflate around the proximal end of the flexible catheter body, and a second balloon positioned to inflate around the distal end of the flexible catheter body. The flexible catheter body has a first lumen for allowing a fluid to pass through the catheter during treatment and bypass the treatment area, a second lumen for inflating the first balloon and the second balloon, and a third lumen for passing an agent to an outlet between the first balloon and the second balloon.

The following detailed description is presented to enable any person skilled in the art to make and use the invention. For purposes of explanation, specific nomenclature is set forth to provide a thorough understanding. However, it will be apparent to one skilled in the art that the specific nomenclature and details are not required to practice the invention. Descriptions of specific applications are provided only as representative examples. Various modifications to the embodiments will be readily apparent to one skilled in the art, and the general principles defined herein may be applied to other embodiments and applications without departing from the scope of the invention. Thus, the present invention is not intended to be limited to the embodiments shown, but is to be accorded the widest possible scope consistent with the principles and features disclosed herein.

Figure 1B:
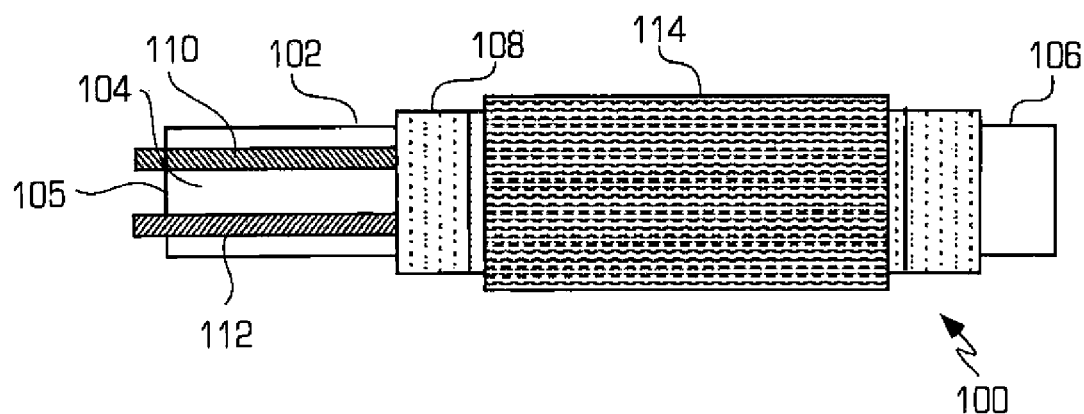
Figure 1C:
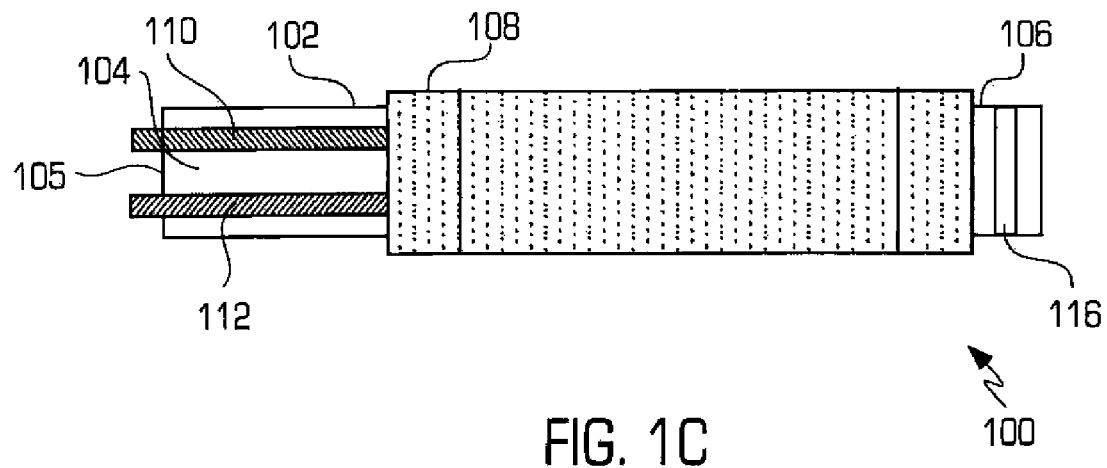

With reference now to FIGS. 1A-1C, various embodiments of the multi-function catheter of the present invention will be described. As will be described in more detail below, the multi-function catheter may be used for removal of arterial plaques; installation of a stent, infusion of drugs; sealing off an aneurysm or a branch of a vessel; dilation of a biological path; and other usages.

As shown in FIG. 1A, a multi-function catheter, generally designated by the reference number 100, has a flexible tubular catheter body 102 having an inner lumen 104, a proximal end 105, and a distal end 106; an inflatable balloon assembly 108 that is capable of multi-stage inflation at the distal end 106 of the catheter body 102; at least one fluid delivery conduit 110 that is adapted to permit a biological fluid (e.g., blood) flow through a path; and at least one balloon control conduit 112 that inflates and deflates the balloon assembly 108. The multi-function catheter 100 may further include a pre-manufactured stent 114 on the outer periphery of the balloon assembly 108, as illustrated in FIG. 1B, and/or a magnetized metal 116 at the distal end 106 of the catheter body 102, as illustrated in FIG. 1C. The magnetized metal 116 allows an operator of the multi-function catheter 100 to move the catheter 100 through a biological path to a target site by a magnetic field, e.g., in conjunction with 3D imaging. The biological path includes, but is not limited to, blood vessels, respiratory tracts, urinary tracts, gastrointestinal tracts, reproductive tracts, and biliary ducts. In a preferred embodiment, the multi-function catheter 100 is approximately 0.03 to 0.07 inches in diameter. The absolute dimensions of the multi-function catheter 100 chosen for a particular procedure depend on the location of the target site and the size of the biological path used to access the target site, as is well understood to those skilled in the art.

Figure 2A:
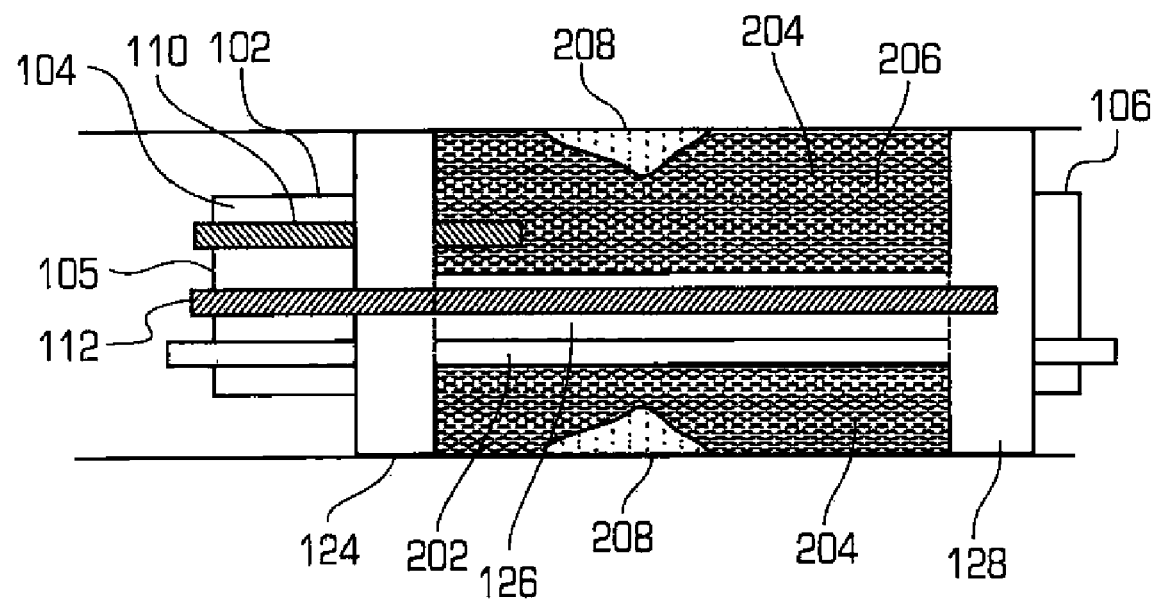
FIGS. 2A and 2B illustrate a side-sectional view of an embodiment of a multi-function catheter with an inflated balloon, and a cross-sectional view of the proximal end of the multi-function catheter, respectively.
Figure 2B:
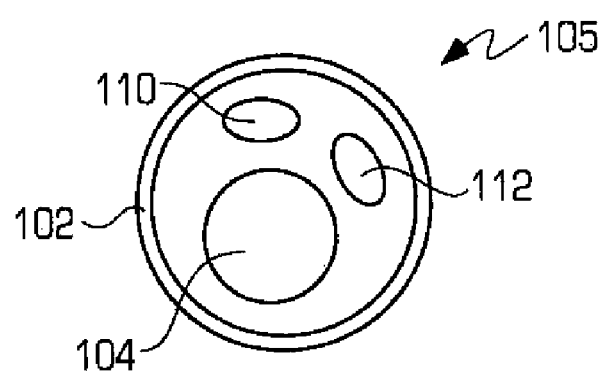

With reference now to the sectional views in FIGS. 2A and 2B, the catheter body lumen 104 allows a guide wire 202 to enter at the proximal end 105 and exit at the distal end 106. The body lumen 202 also allows blood to flow through the catheter 100 during a procedure. Typically, the guide wire 202 is placed into a biological path and advanced beyond a treatment site. Then the catheter 100 is placed over the guide wire 202 and advanced to the treatment site, guided thereto using the trajectory of the prelaid guide wire 202. Various types of guide wires may be used. For example, a metal wire generally made of nickel, preferably of 0.018 inch diameter or smaller, may be used. Guide wire 202 may be removed and replaced during a treatment procedure.

With further reference to FIG. 2A, the balloon assembly 108, when inflated, has at least three balloon elements: a proximal balloon element 124, a central balloon element 126, and a distal balloon element 128. The central balloon element 126 can be inflated to at least two different stages. In one embodiment, the three balloon elements 124, 126 and 128 are integrated parts of the balloon assembly 108 and are controlled collectively by the balloon control conduit 112. In another embodiment, the central balloon element 126 can be individually controlled by the balloon control conduit 112. In yet another embodiment, each of the three balloon elements can be individually controlled by the balloon control conduit 112. The individualized control allows one balloon element to be inflated or deflated without affecting the inflation status of the other balloon elements in the balloon assembly 108. As shown in FIG. 2A, the proximal balloon element 124 and the distal balloon element 128, when inflated, form a chamber 204 between the balloon assembly 108 and an arterial wall 206 around a plaque 208. The volume of the chamber 204 may be adjusted by inflating the central balloon 126 to different stages.

The catheter body 102 can be prepared from any of a number of readily available, non-toxic, flexible polymers including, for example, polyolefins such as polyethylene or polypropylene and polyvinyl halides such as polyvinyl chloride or polyvinylidene chloride. The balloon assembly 108 can be fabricated from similar materials manufactured so as to be expansible under pressure and with sufficient elasticity to contract when the pressure is released. The dimensions of the balloon elements will be such that they will reach the desired diameters at preset pressures. In a preferred embodiment, the proximal and the distal balloon elements 124 and 128 will reach the desired diameter at a first preset pressure of about 75 mm to 150 mm Hg and hold the dimensions even if the pressure is increased to as high as 15 atmospheres, while the central balloon element 126 will reach a first diameter at the first preset pressure and other diameters at other preset pressures.

The absolute dimensions selected for the balloons will depend upon the diameter of the vessel involved in the treatment. In one embodiment, the proximal and the distal balloon elements 124 and 128 are from about 0.3 mm to about 10 mm in length and their expanded diameters may be in approximately the same range. The shape of the inflated balloons may be conical, spherical, square, or any shape that is convenient for the particular application. The central balloon 126 is inflatable to the same diameter range as the proximal and the distal balloons 124 and 128, but the length is preferably from about 0.4 to 2 inches.

With reference again to FIGS. 2A and 2B, the fluid delivery conduit 110 and the balloon control conduit 112 are formed within the catheter body 102. The fluid delivery conduit 110 includes one or more fluid delivery channels for allowing fluids and/or gases (hereinafter referred to as fluids) to flow into and/or out of the chamber 204. As is understood by one skilled in the art, more than one fluid delivery conduit 110 may be formed within the catheter body 102. The balloon control conduit 112 also includes one or more channels for allowing the inflation material to flow into or out of the inflatable balloon assembly 108 for the inflation/deflation of the balloon assembly 108. The inflation material may be any liquid or gas that would be safe for the treatment subject even if there is a leakage, such as a saline solution. The fluid delivery conduit 110 and the balloon control conduit 112 may be formed using Teflon, polyurethane, polyethylene, or other similar materials.

Figure 3:
FIG. 3 is a flow diagram showing a method for treating arterial plaque using a multi-function catheter pursuant to the principles of the present invention.

With reference now to FIG. 3 of the drawings, there is illustrated a method, generally designated by the reference number 300, for treating arterial plaque using the multi-function catheter of the present invention. First, the multi-function catheter 100 is advanced to the plaque site (step 302). Second, the balloon assembly 108 is inflated to create a perfusion chamber around the plaque (step 304). Third, a plaque removal agent is perfused into the perfusion chamber to dissolve or digest the plaque (step 306). Fourth, a stent is placed at the treatment site to prevent restenosis (step 308). In one embodiment, the stent is formed using a fluent composition that is transformed into a non-fluent composition in situ at the treatment site. In another embodiment, the stent is pre-manufactured and is part of the multi-function catheter 100, as shown in FIG. 1B. Finally, the multi-function catheter 100 is withdrawn and the stent is left behind to assist the cell wall in healing at the treatment site (step 310).

Figure 4A:
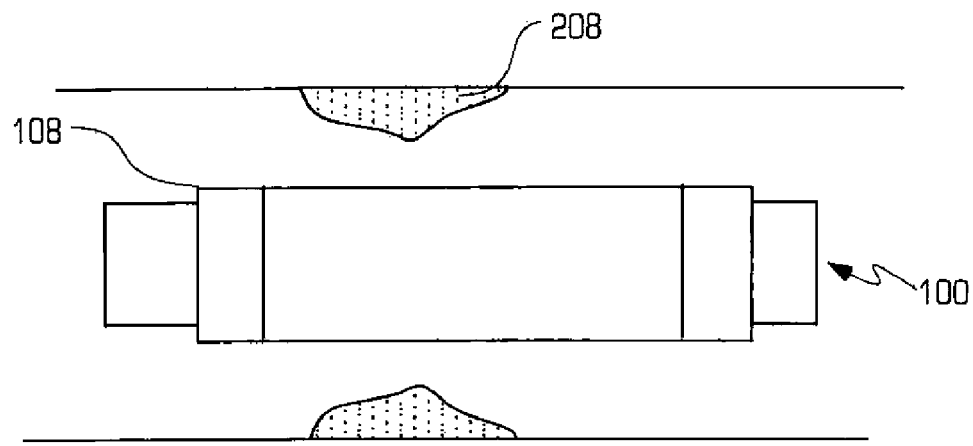
FIGS. 4A-4E generally depict a procedure for plaque removal and stent installation using a multi-function catheter as set forth in the present invention.
Figure 4B:
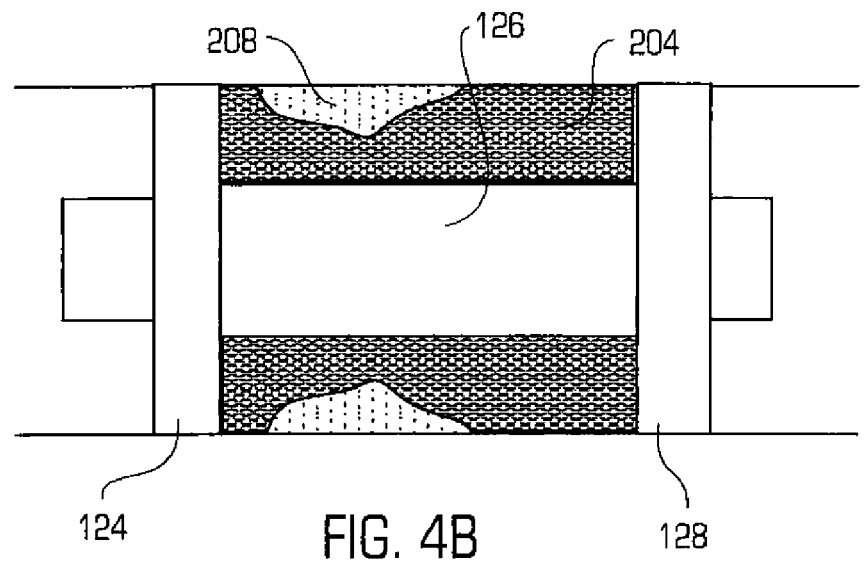

The treatment process is further illustrated in FIGS. 4A-4E. As shown in FIG. 4A, the multi-function catheter 100 is advanced to the treatment site so that the balloon assembly 108 is located right inside the area of the plaque 208. The balloon assembly 108 is then inflated to a first stage to form a chamber 204 around the plaque 208 (FIG. 4B). A plaque removal agent is then delivered within the chamber 204. The plaque removal agent can be forced into the plaque by the application of pressure through the fluid delivery conduit 110 (shown in FIG. 2A) or by the expansion of the central balloon element 126, as discussed in more details hereinabove. The plaque removal agent can also be recirculated into the chamber 204 until the plaque (mostly cholesterol) is dissolved.

Figure 4C:
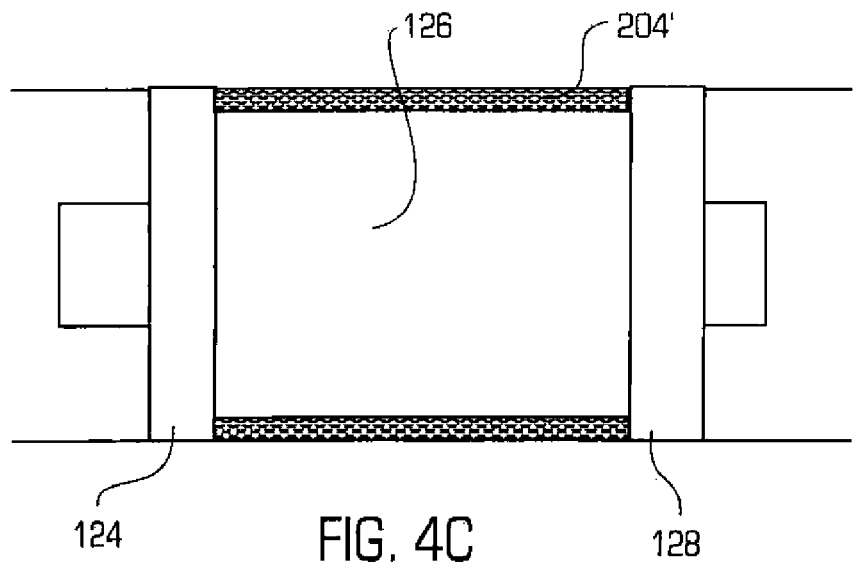
Figure 4D:
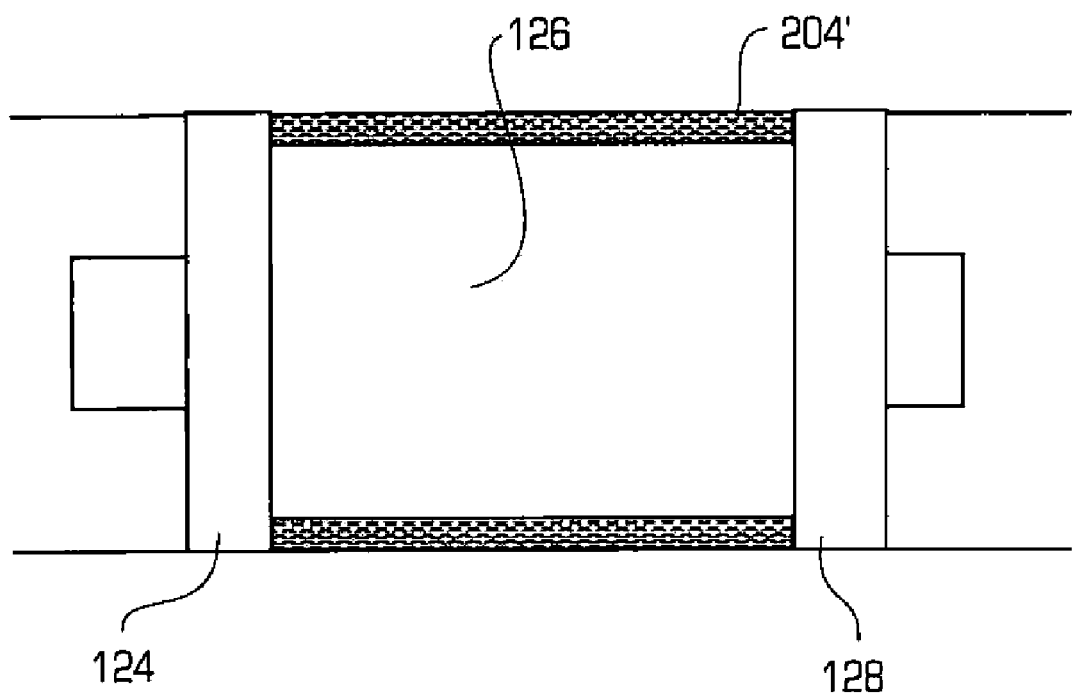
Figure 4E:

After the desired effect is obtained, the chamber 204 is then washed with a washing solution such as saline in order to remove any traces of the plaque removal agent. In the next step, the balloon assembly 108 is inflated to a second stage (FIG. 4C). At this stage, most of the space vacated by the plaque 208 is taken up by the further inflated balloon assembly 108. The much smaller chamber, designated by the reference number 204', now serves as a mold for the formation of a customized stent. As shown in FIG. 4D, the chamber 204' is filled with a fluent pre-stent composition delivered through the fluid delivery conduit 110 (shown in FIG. 2A). The pre-stent composition solidifies in the chamber 204' to form a stent 210. The balloon assembly 108 is then deflated and the multi-function catheter 100 is withdrawn, leaving behind the stent 210 at the treatment site (FIG. 4E). In a preferred embodiment, the stent 210 may contain or be coated with a material to reduce the occurrence of restenosis and clotting. In another preferred embodiment, the chamber 204' defines a streamlined shape for the stent 210 so that the risk of blood clot over the stent 210 is reduced.

With regard to the plaque removal process of FIG. 4B, various types of plaque removing agents may be used with the multi-function catheter 100. In general, the plaque removing agent should be non-toxic and should not cause clotting of the blood. Because of the low volumes involved, e.g. about 0.1 to about 0.5 ml, a number of polar organic solvents can be employed to dissolve cholesterol and its esters, even though this would normally be considered too toxic for internal use. These organic solvents include, for example, acetone, ether, ethanol, and mixtures thereof.

The plaque removing agent may also include isotonic aqueous buffers containing phospholipids. Phospholipids are naturally available compounds which on hydrolysis yield fatty acids; phosphoric acid; an alcohol, usually glycerol; and a nitrogenous base such as choline or ethanolamine. Examples of phospholipids include lecithins, cephalins and sphingomyelins. The efficiency of the plaque removing agent containing lecithin or other phospholipid can be improved by the addition of bile acids such as cholic, deoxycholic, chenodeoxycholic, lithocholic, glycocholic and taurocholic acid.

The plaque removing agent may also include an enzyme or a mixture of enzymes. In one embodiment, the enzyme is a pancreatic cholesterol esterase that hydrolyzes cholesterol into sterol and fatty acids. In another embodiment, the enzyme is a collagenase. The collagenase cleaves collagen which is the main supportive structure of the plaque. The plaque body then collapses. Other enzymes such as papain, chymotrypsin, chondroitinase and hyaluronidase may also be employed together with the collagenase or as an alternative thereto. The enzymes may be used either with or without bile acid or phospholipid. The enzyme may be solubilized in a number of physiologically acceptable buffers including phosphate buffered saline, tris buffer, Ringer's lactate buffer and the like.

In a preferred embodiment, a fluid delivery system, preferably with multiple fluid delivery channels, is used. Usually, an automatic machine is used to perfuse the chamber 204 with the plaque removing agent through the fluid delivery conduits 110. Similarly, the inflation and deflation of the balloon assembly 108 can be controlled by an automatic machine connected to the balloon control conduit 112.

Various fluent materials may be used to form the stent 210 in situ. The fluent pre-stent composition can be formulated from any one or more components which have the necessary biocompatible properties and which can be converted in situ to a solid stent composition. Typically, the liquid-to-solid phase transformation is triggered by the introduction of a chemical catalyst and/or energy, such as RF energy or microwave energy. Materials capable of this phase transformation are discussed in detail in U.S. Pat. No. 5,899,917, which is hereby incorporated by reference.

The pre-stent composition may also contain a protein and/or a polysaccharide. Examples of the protein/polysaccharide component include, but are not limited to, collagen, fibrin, elastin, fibronectin, vitronectin, aglin, albumin, laminin, gelatin, cellulose, modified cellulose, starch, modified starch, synthetic polypeptide; acetylated, sulfonated and phosphorylated collagen, and glycosaminoglycans (heparin, heparan, dermatan, chrondoin sulfate).

The pre-stent composition may contain an aqueous electrolyte solution with sufficient ionic strength to conduct electric current or RF energy. The pre-stent composition may also contain a reinforcement agents and adjuvants to promote wound healing. Examples of the reinforcement agent include, but are not limited to, poly(lactide), poly(glycolide), poly (lactide)-co-(glycolide), poly (caprolactone), poly (betahydroxtbutylate), a poly (anhydride), and a poly (orthoester).

The pre-stent compositions may also contain materials that have a high susceptibility and absorbance for microwave energy. Such materials include, but are not limited to, metal oxides, such as ferric oxide, and carboniferous materials, such as acetylene black and graphite, or hydroxyl containing materials, such as alcohols or water.

If the pre-stent composition solidifies by forming covalent bonds mediated by free radical species, a thermally-activated free radical initiator and/or an accelerator may be included in the composition. Such thermal initiation materials include, but are not limited to, a peroxide material like benzoyl peroxide or lauroyl peroxide or ammonium persulfate, or an azo material, such as azo bis(isobutylnitrile) (AIBN, Vazo 64). Accelerator materials include, but are not limited to, reductants such as amines, like triethanol amine (TEOA), alpha hydroxy ketones, like benzoin and acetoin, and ascorbic acid and derivatives.

The pre-stent material can be mixed with therapeutic agents to promote healing and prevent restenosis. Examples of the therapeutic agents include, but are not limited to, immunosuppressant agents such as cyclosporin, adriamycin, and equivalents; anticoagulants such as heparin, anti-platelet agents, fibrinolytic and thrombolytic agents; anti-inflammatory agents; and growth factors. Alternatively, the stent 210 may be coated with a material to reduce restenosis and clotting.

The stent composition may also be formed of a bioresorbable material and itself be bioreabsorbed into the surrounding tissue.

The multi-function catheter 100 of the present invention can also be used to treat aneurysms. As described earlier, treatment using an endovascular coil system is often time-consuming and requires experienced operators. The multi-function catheter of the present invention offers an relatively simple and quick alternative treatment for aneurysms, which is particularly useful in an emergency setting.

Figure 5:
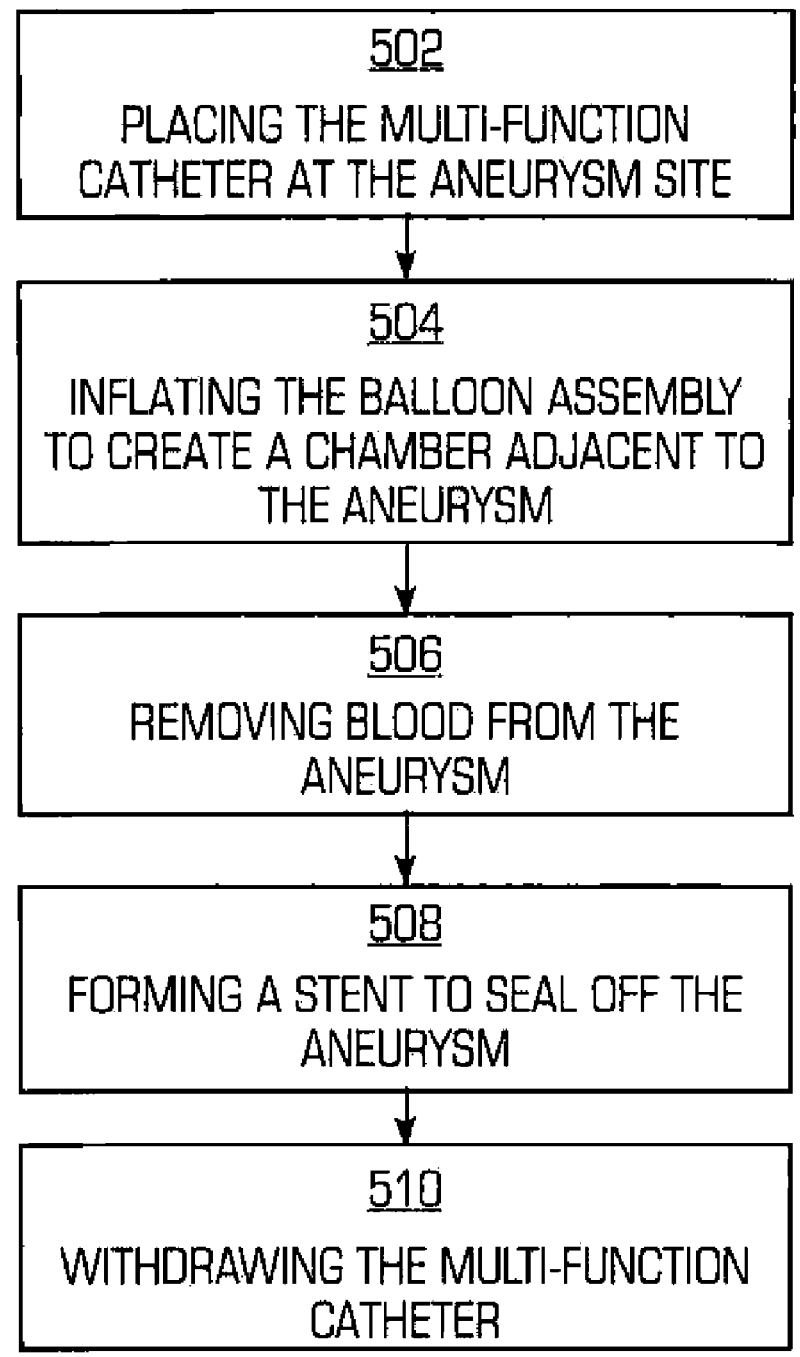
FIG. 5 is a flow diagram showing a method for treating aneurysms using a multi-function catheter pursuant to the principles of the present invention.

With reference now to FIG. 5, there is illustrated a flow diagram of a method, generally designated by the reference number 500, for treating aneurysms using the multi-function catheter 100 of the present invention. First, the multi-function catheter 100 is advanced to the aneurysm site (step 502). The balloon assembly 108 is then inflated to create a chamber around the area weakened by the aneurysm (step 504). The blood in the aneurysm can be removed through the fluid delivery conduit 110 (shown in FIG. 2A) to prevent vasospasms and hydrocephalus (step 506). A stent is then placed around the weakened area to seal off the aneurysm (step 508)

and the multi-function catheter is withdrawn (step 510). As described earlier, the stent may be a pre-manufactured stent or be formed in situ.

Figure 6A:
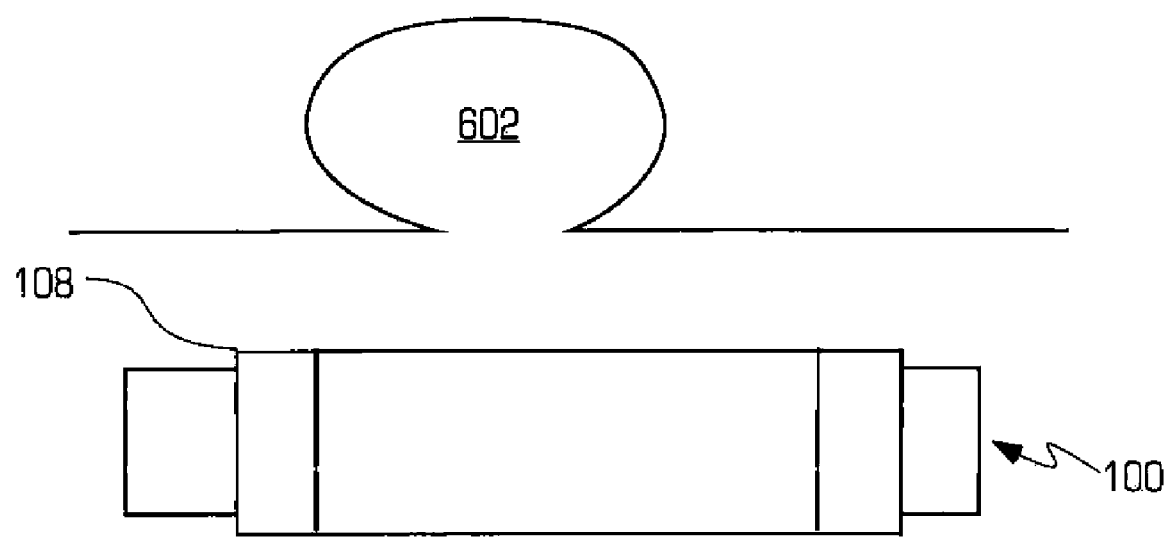
FIGS. 6A-6D generally depict a treatment process for aneurysms using a multi-function catheter as set forth in the present invention.
Figure 6B:
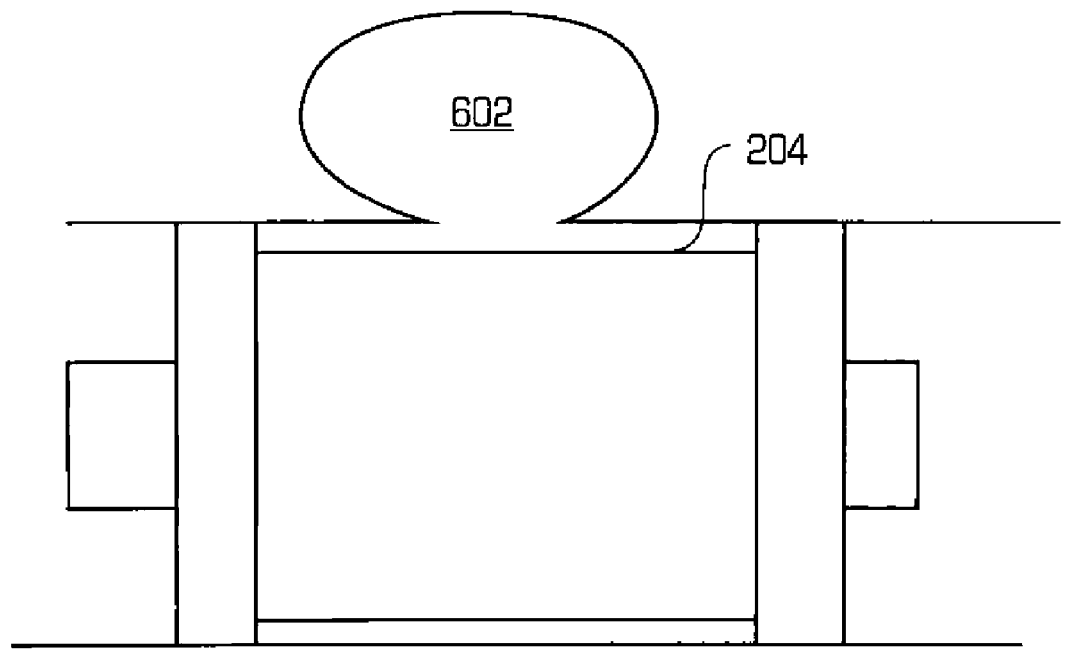
Figure 6C:
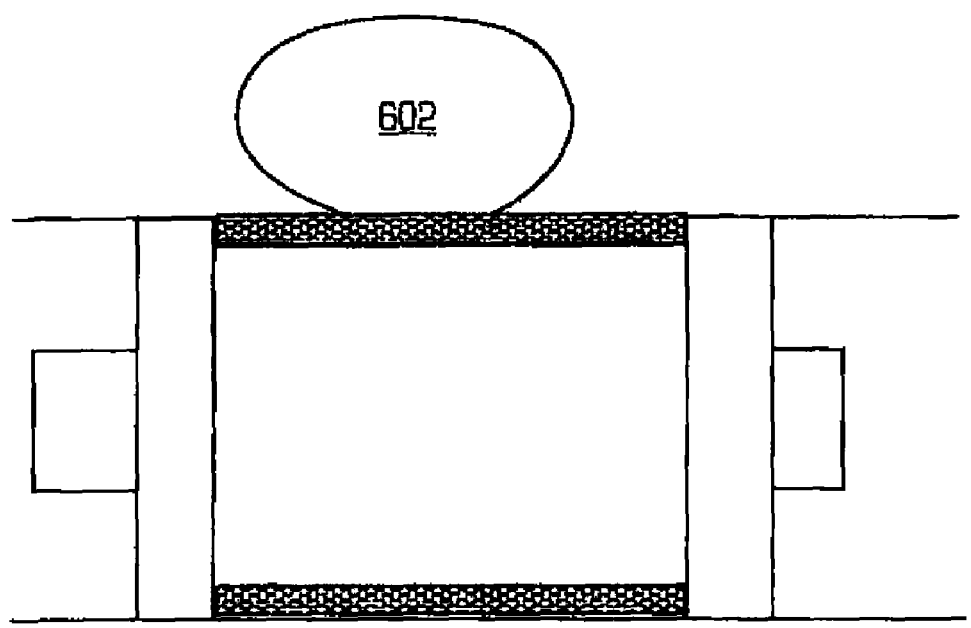
Figure 6D:
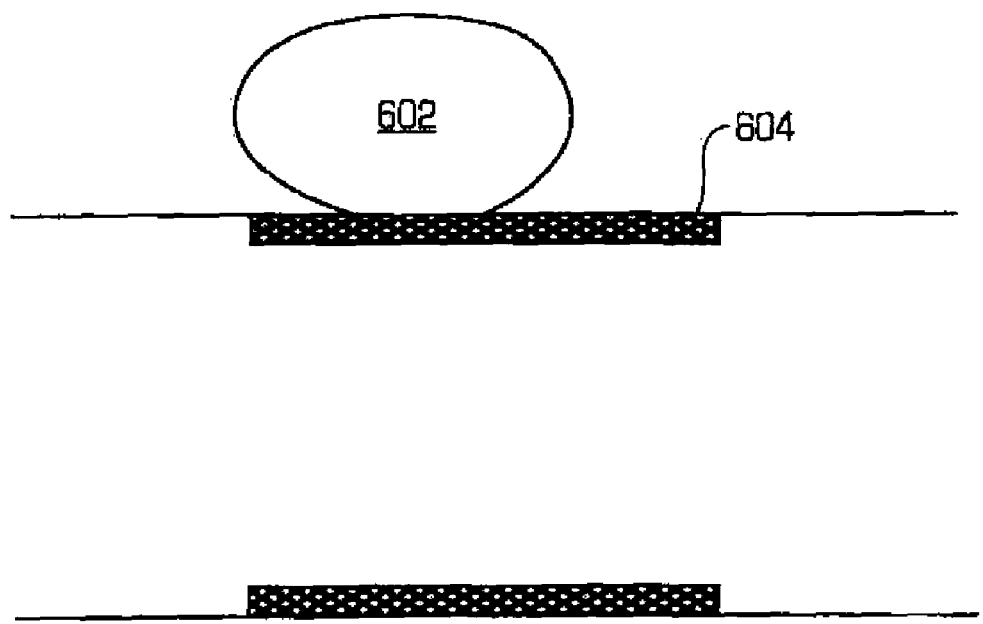

The treatment process set forth hereinabove in connection with FIG. 5 is further illustrated in FIGS. 6A-6D. As shown in FIG. 6A, the multi-function catheter 100 is advanced to the treatment site so that the balloon assembly 108 is placed in the area weakened by the aneurysm 602. The balloon assembly 108 is then inflated to form a chamber 204 adjacent to the aneurysm 602 (FIG. 6B). A negative pressure may be created inside the chamber 204 by the fluid delivery conduit 110 in order to remove the blood from the aneurysm 602. A stent 604 is then formed at the area weakened by the aneurysm 602 (FIGS. 6C and 6D). In an emergency, a pre-manufactured stent may be installed to quickly seal off the aneurysm 602. As readily realized by one skilled in the art, the method 500 can be used for almost any aneurysm in the body.

The multi-function catheter 100 of the present invention can also be used for oncology purposes. Using the endovascular catheter of the invention results in a treatment that is effectively targeted to a vascular tumor because the catheter is able to get very close to the tumor without impairing the blood supply to other organs. The endovascular catheter is placed within the one of the principal vessels feeding the tumor. The tumor is connected to the principal vessel via one or more branch vessels, and the bloodflow through the branch vessels keep the tumor sustained (e.g., by delivering oxygen and nutrients to the tumor cells). The endovascular catheter of the invention causes necrosis of the tumor by pumping an anti-tumor agent or saline solution through the branch vessels, killing the tumor either chemically or through hypoxia.

Figure 7:
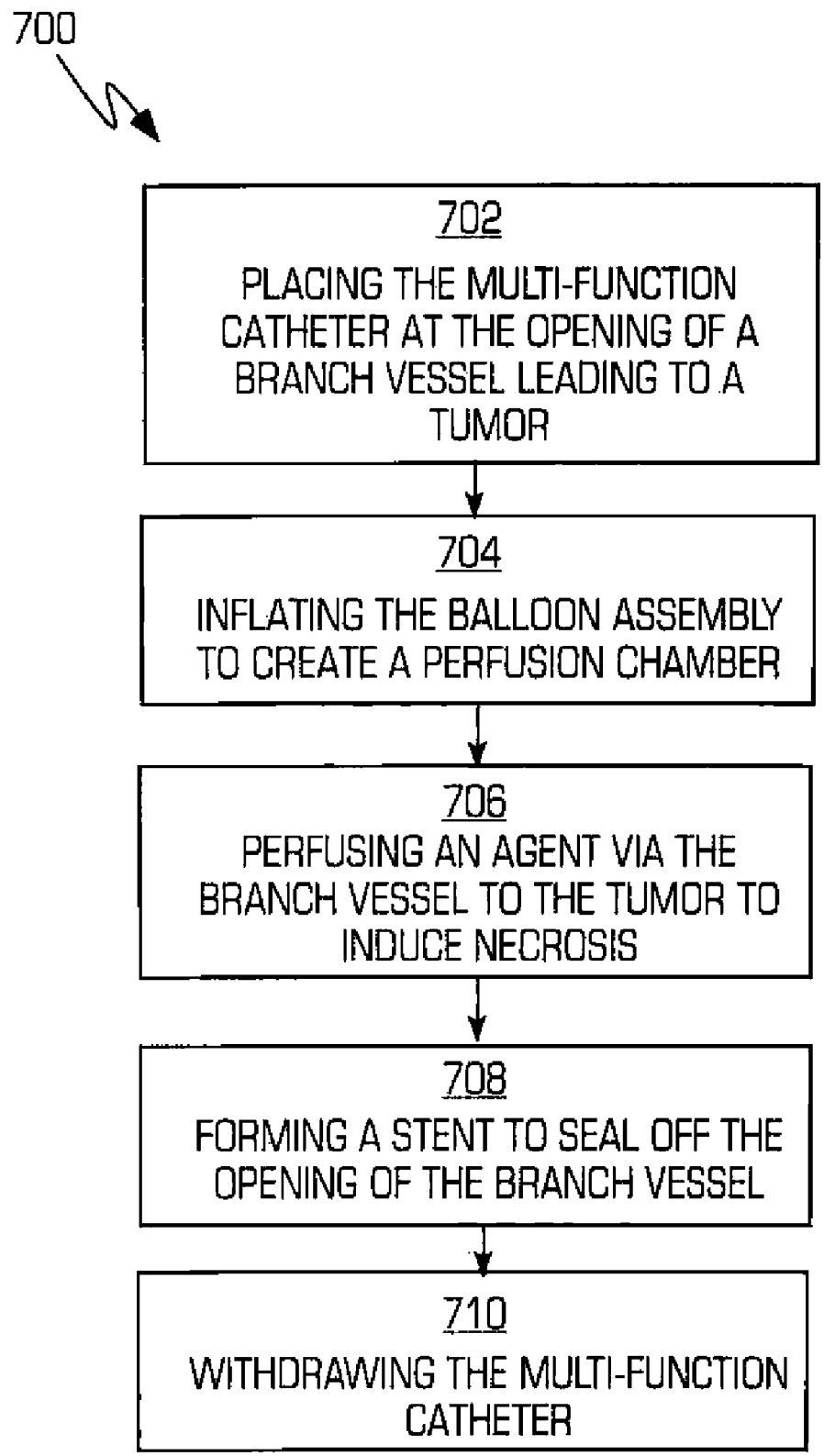
FIG. 7 is a flow diagram showing a method for treating tumors using a multi-function catheter pursuant to the principles of the present invention.

With reference to FIG. 7, there is illustrated a flow diagram of a method, generally designated by the reference number 700, for treating tumors using the multi-function catheter 100 of the present invention. In this procedure, the multi-function catheter is advanced to the opening of a branch vessel that provides blood supply to a tumor (step 702). The balloon assembly is then inflated to create a chamber around the opening of the branch vessel (step 704) the tumor is perfused with an agent via the branch vessel to induce necrosis (step 706). Optionally, a stent is formed at the opening of the branch vessel to cut off the blood supply to the tumor after the perfusion (steps 708 and 710). The method 700 thus allows direct targeting of the tumor with an anti-tumor agent and minimizes side effects.

Figure 8A:
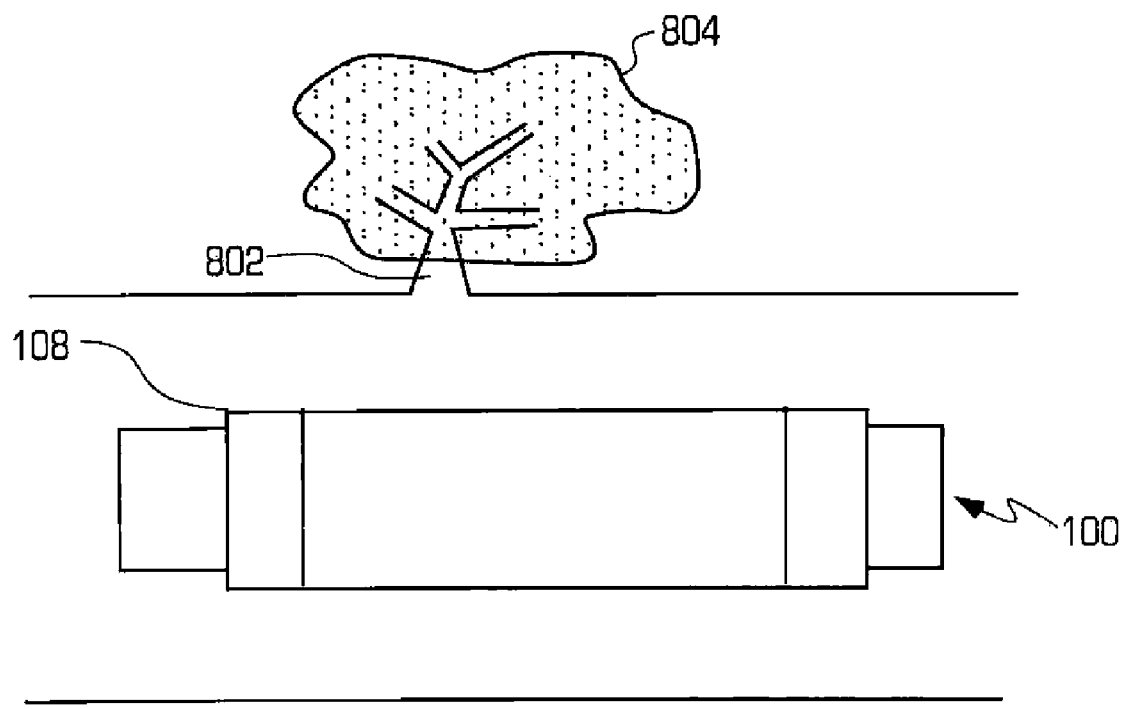
FIGS. 8A-8D generally depict a process of oncology treatment using a multi-function catheter as set forth in the present invention.
Figure 8B:
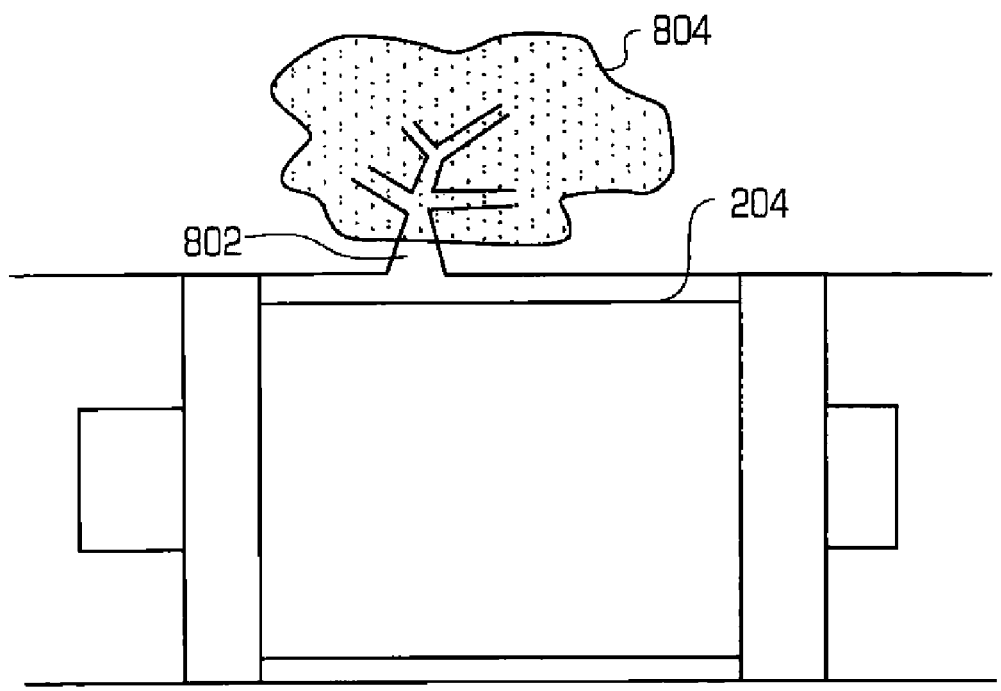
Figure 8C:
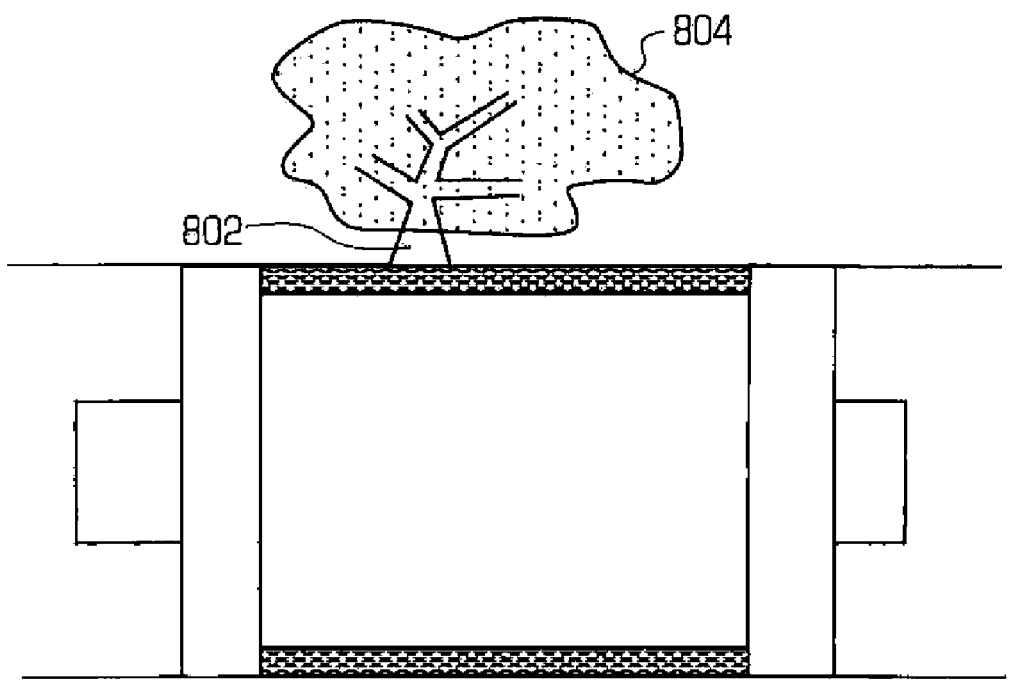
Figure 8D:
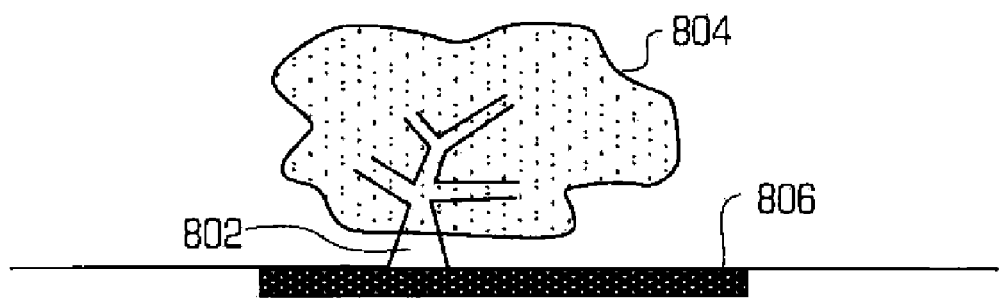

The treatment process set forth hereinabove in connection with FIG. 7 is further illustrated in FIGS. 8A-8D. As shown in FIG. 8A, the multi-function catheter 100 is advanced to the treatment site so that the balloon assembly 108 is placed near the vessel opening 802 of a branch artery that provides blood to a tumor 804 or other deleterious tissue. The balloon assembly 108 is then inflated to form a chamber 204 around the vessel opening 802 (FIG. 8B). The tumor 804 is then perfused with an agent through the branch artery to induce necrosis of tumor cells. In one embodiment, the agent is a saline solution. The replacement of blood with saline induces ischemic necrosis of tumor cells. In another embodiment, the agent is an anti-tumor agent that is toxic to tumor cells. After the infusion, a stent 806 may be formed at the vessel opening 802 to seal off the branch artery and cuts off the blood supply to the tumor 804 (FIGS. 8C and 8D).

Figure 9:
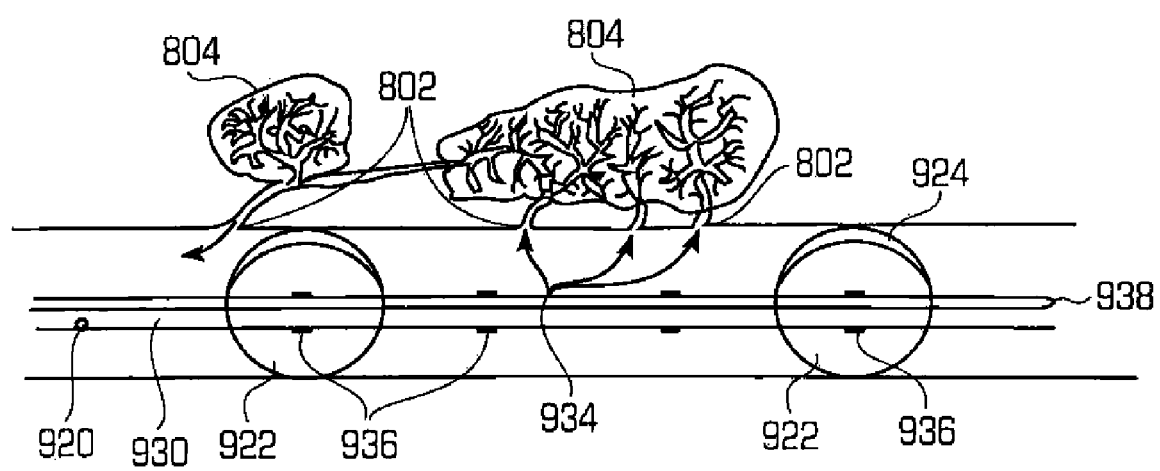
FIG. 9 illustrates an alternative embodiment of the multi-function catheter.

FIG. 9 is an alternative embodiment of the multi-function catheter, shown as a catheter 920. This multi-function catheter 920 has a proximal balloon element 922 and a distal balloon element 924 but no central balloon element (it could be there but just not inflated). As shown in FIG. 9, the proximal and distal balloon elements 922, 924 are inflated in a blood vessel 101. The blood vessel 101 has openings 802 through which the tumor 804 draws blood and receives oxygen. The balloon elements 922, 924 are positioned so that they stop the blood from circulating to the vessel openings 802.

The catheter 920 includes a catheter body 930, which is similar to the flexible catheter body 102 shown in FIG. 2B. The catheter body 930 may be made of aliphatic polyurethane such as the commercially available Tecoflex EG68D. Like the flexible catheter body, the catheter body 930 is preferably flexible and has lumens extending through it. For example, since it is undesirable to cut off the circulation of a biological fluid (e.g., blood), there is a fluid bypass lumen that provides a bypass for the biological fluid. Although not shown, the inlet and outlet of the fluid bypass lumen are somewhere on the catheter body 930 outside the region defined by the balloon elements 922, 924. For example, there is a first opening that is proximal to the balloon assembly and a second opening that is distal to the balloon assembly. In addition, there is a fluid delivery conduit for delivering the agent to the chamber formed by the balloon elements 922, 924, and a balloon control conduit for controlling the inflation levels of the balloon elements 922, 924. The balloon control conduit extends from its inlet to a proximal outlet in the balloon element 922 and a distal outlet in the balloon element 924 so that both balloons are inflated and deflated through the same lumen. The fluid delivery conduit extends from its inlet to an outlet 934 that is positioned between the two balloon elements 922, 924. There may be one or more outlets 934 for the fluid delivery conduit. The shape of the outlet 934 may be varied. For example, the outlet 934 may be rectangular (as shown), round, oval, trapezoidal, etc.

As the balloon elements 922, 924 are inflated, a treatment area including the tumor 804 becomes isolated. A chemotherapy agent and an imaging agent are added to the isolated area between the balloon elements 922, 924. To achieve the isolation, the imaging agent is added to the space between the balloon elements 922, 924 while the balloon elements 922, 924 are being simultaneously inflated. This way, a user knows that the inflation should be stopped when no more imaging agent leaks out of the isolated area. The imaging agent and a chemotherapy agent is then added to the isolated area and forced into the tumor 804. The chemotherapy agent is held in contact with the tumor 804 as long as necessary. An embolic material (e.g., polyvinyl alcohol) in the form of gels or foams may be added so that they are pushed into the tumor to help cut off blood flow to the tumor 804.

As more agent is added to the chamber between the balloon elements 922, 924, more of it will be delivered to the tumor 804, as shown by the arrows from the outlet 934. The agent enters the tumor instead of the blood, but does not carry oxygen like the blood. Thus, as the agent flows through the tumor, the tumor experiences hypoxia. The agent that is fed to the tumor 804 circulates through the tumor 804 and exits the tumor 804 through another vessel opening 802. The amount of the agent that is fed to the tumor 804 is insignificant enough that the addition of the circulated agent to the blood stream does not cause any adverse side effects.

The multi-purpose catheter 920 has markers 936 on its outer surface and a radiopaque tip 938. The markers 936 and the radiopaque tip 938, which may be made of the same material (e.g., platinum iridium), can be seen with an imaging device, and are useful for proper placement of the catheter 920.

When inflated, the balloon elements 922, 924 have a maximum diameter of about 4-8 mm, the actual diameter being adjusted to the size of the blood vessel 101. The balloon elements 922, 924 may be made of polyurethane or silicon urethane of about 0.001-inch thickness, or of polyisoprene. The balloon elements 922, 924 may be manufactured as components that are separate from the flexible catheter body 930 but designed to slip over the flexible catheter body 930. The same markers 936, which protrude relative to the catheter body 930, indicate the positions of the balloon elements 922, 924 (which varies depending on the specific application) and holds the balloon elements 922, 924 in place. In the embodiment shown, the markers 934 are between the balloon elements 922, 924 and in the balloon elements 922, 924. However, the number of markers and their positions may be adjusted to the application.

FIG. 9 depicts the balloon elements 922, 924 in their inflated state. When not inflated, the balloons are positioned around the catheter body 102 in fixed locations. When the balloon elements 922, 924 are inflated, the center portion becomes larger while the end portions remain adhered to the catheter body 102 to hold the inflated portion in place.

FIG. 10 is a flow diagram of a method 900 for treating an area (e.g., a tumor) using an embodiment of the multi-function catheter of the invention, such as the catheter shown in FIG. 10 below. The catheter 100 is placed at an area of treatment (step 902), for example by using the radiopaque tip and markers through an imaging device. Once the catheter is properly positioned, the balloon assembly on the catheter is inflated to create a space between the balloon elements 922, 924 (step 904). Then, an agent (e.g., an anti-tumor agent, saline solution) is delivered to this space through a lumen extending through the catheter (step 906). After the agent has been delivered for a desired period of time, the agent delivery is stopped and the balloon elements 922, 924 are deflated (step 908). The catheter 100 is then withdrawn from the area of treatment (step 910).

The use of saline solution to kill the tumor through hypoxia is described above. In methods 700 and 900, a variety of anti-tumor agent may be used instead of saline solutions to chemically kill the tumor. The anti-tumor agent can be any commonly used chemotherapy agent, such as alkylating agents, vinca alkaloids, anthracycline antibiotics, glucocorticoids, and inhibitors of protein/DNA/RNA synthesis. A lower concentration of the chemotherapy agent can be used in this invention than in the conventional chemotherapy treatments without compromising the effectiveness because in this method, the agent is provided to the tumor in a targeted manner. The exact concentration of the chemotherapy agent that is used depends on the type of chemotherapy agent. The saline solution or the anti-tumor agent may be combined with an imaging agent (e.g., barium sulfate) so that the infusion of the saline or the anti-tumor agent into the tumor can be observed and carefully controlled. The imaging technology that may be used with the multi-function catheter 100 is well known.

The multi-function catheter may also be used in a number of other procedures. For example, the multi-function catheter can be used to permanently open a constricted vessel passage, such as constricted tracheobronchial or a partially blocked fallopian tube, by dilating the constructed vessel passage and installing a stent in the constricted area. The multi-function catheter can also be used for the treatment of trauma patient. Specifically, the multi-function catheter may be used to stop bleeding or to remove blockage in vessels in a wounded tissue.

Figure 11:
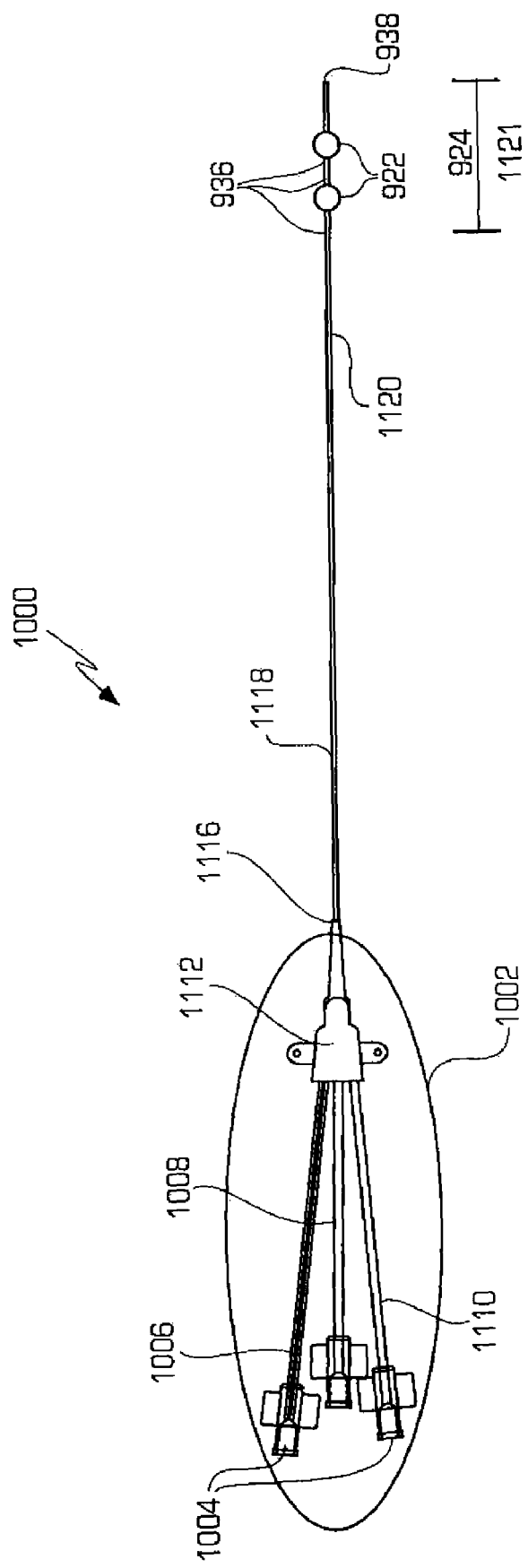
FIG. 11 illustrates another embodiment of the multi-function catheter.

FIG. 11 illustrates another embodiment of the multi-function catheter 1000. In this embodiment, the catheter may be made of similar material as described above and may include the proximal and distal balloons 922, 924 as shown in other embodiments. The central balloon shown in the other embodiments may be uninflateable in this embodiment or it may be non-existent so that the multi-function catheter is this embodiment has two or three balloons. The multi-function catheter shown in FIG. 11 may be used to perform the same procedures and methods described above for the other embodiments. In this embodiment, the multi-function catheter 1000 may also comprise a proximal portion 1002 that has one or more female leurs 1004, an infusion branch extension 1006, a guidewire branch extension 1008, a balloon branch extension 1010, a manifold 1112 and a protective molded sleeve 1116. The multi-function catheter may also have a catheter (with two or more lumens as described below in more detail) that extends from the proximal portion 1002 and has a proximal extrusion 1118 and a distal extrusion 1120. The multi-function catheter in this embodiment may be 171-181 cm from the proximal portion 1002 to the end of the catheter and 150-154 cm from the end of the proximal portion 1102 to the end of the catheter.

The multi-function catheter may also have a treatment portion 1121 to deliver a treatment material/agent or treatment to the treatment site that is described below with reference to FIGS. 18-21. The multi-function catheter may also have, at its distal end, the proximal and distal balloons 922, 924, that may be made of silicon, one or more marker bands 936 as described above and the radiopaque tip 938 as described above. The multi-function catheter, once situated at a treatment site, allows the balloons 922, 924 to be inflated (using the balloon branch extension to direct a balloon inflation material to the balloons) to isolate a treatment site as described above and then deflated when the treatment is complete, allows a treatment material/agent (as described above) to be infused into the treatment site (through the infusion branch extension 1006) and allow a guidewire to be used to guide the catheter to the treatment site.

FIG. 12 illustrates more details of the proximal portion 1002 of the multi-function catheter shown in FIG. 11. Each luer 1004 may be a 0.080" ID female luer that may be made of polycarbonate. For example, a luer made by Qosina, Inc. in Edgewood. N.Y. (part number 65262) may be used for the multi-function catheter. The proximal portion 1002 may include an infusion luer 1104a connected to the infusion branch extension 1106 that allows a doctor, surgeon, nurse, medical personnel to connect a treatment material/agent to the luer and then infuse the treatment material/agent into the treatment site through the multi-function catheter. The proximal portion 1002 also may include an guide wire luer 1104b connected to the guidewire branch extension 1108 that allows a doctor, surgeon, nurse, medical personnel to direct a typical guidewire into the multi-functional catheter so that the multi-function catheter may be positioned at the treatment site. The proximal portion 1002 also may include a balloon luer 1104c connected to the balloon branch extension 1110 that allows a doctor, surgeon, nurse, medical personnel to connect an inflation material to the multi-function catheter and then control the inflation/deflation of the proximal and distal balloons (that may be controlled individually or together). The proximal portion 1002 also includes the manifold 1112 that connects the guidewire extension 1108 to a guidewire lumen in the catheter, that connects the infusion extension 1106 to a infusion lumen in the catheter and that connects the balloon extension 1110 to one or more balloon lumens in the catheter. The manifold 1112 may further comprise suture wings 1130 so that the manifold may be sutured in a particular position to secure it during the procedure.

FIG. 13 illustrates more details of the manifold 1112 that is part of the multi-function catheter shown in FIG. 11. The manifold has a suture wings 1130 and also may include narrowing tip portion 1132 and an inlet 1134 that are surrounded by the protective sleeve which connects to the catheter.

Figure 14A:
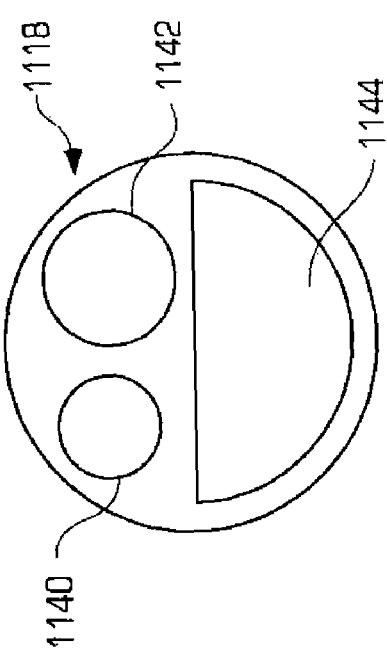
FIGS. 14A and 14B illustrate, respectively, a proximal extrusion and a distal extrusion of the multi-function catheter shown in FIG. 11.
Figure 14B:
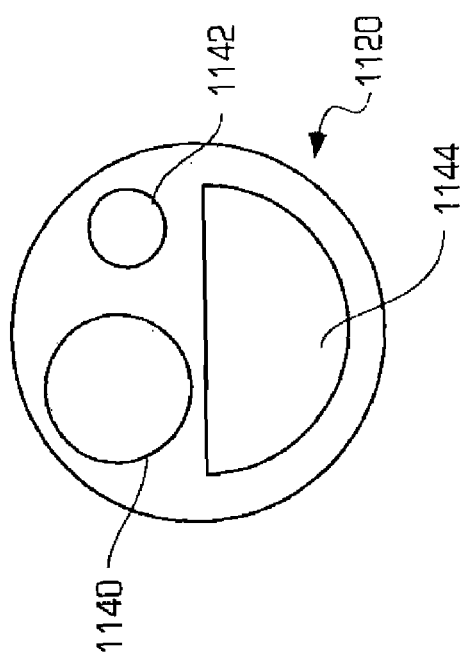

FIGS. 14A and 14B illustrate, respectively, the proximal extrusion 1118 and the distal extrusion 1120 of the multi-function catheter shown in FIG. 11. The catheter forms a continuous pathway from the proximal portion 1002 to the tip 938 for one or more lumens. As shown in FIGS. 14A and 14B, in this embodiment, the catheter may have a guidewire lumen 1140, an infusion lumen 1142 and an inflation lumen 1144 wherein the guidewire lumen accommodates the guidewire that is inserted into the catheter to move the catheter to the treatment site, the infusion lumen carries treatment material/agent to the treatment site and the inflation lumen carries an inflation material, such as saline for example, to the balloons 922, 924 to control the degree of inflation of the balloons. In this example, both of the balloons 922, 924 are inflated/deflated using the same inflation lumen. However, in another embodiment, each balloon may be independently controlled with separate lumens. In the embodiment shown in FIGS. 14A and 14B, the wall thickness of the catheter at the proximal and distal portions may be 0.003 mm. The diameter of the catheter at the proximal extrusion 1118 may be 1.17 mm and may be 0.76 mm at the distal end. In one embodiment, the guidewire lumen may be circular with a 0.33 mm diameter throughout the catheter and the infusion lumen may be circular and have a 0.41 mm diameter at the proximal end and a 0.18 mm diameter at the distal end. In one embodiment, the inflation lumen may be shaped like a half-circle as shown in FIGS. 14A and 14B (although it may be other shapes and is not limited to the shape shown in FIGS. 14A and 14B) and may have a radius of 0.51 mm and a width of 1.0 mm at the proximal end and a radius of 0.31 mm and a width of 0.059 mm at the distal end. The inflation lumen is larger than both the guidewire lumen and infusion lumen because it needs to be large enough to allow deflation of the balloons when the treatment is completed. In particular, a maximum of a one psi vacuum can be applied to the inflation lumen (to deflate the balloons) so that the larger inflation lumen is needed to ensure that the balloons can be deflated using only the one psi vacuum. In one embodiment, once the guidewire is removed from the guidewire lumen when the catheter is positioned at the treatment site, a treatment material/agent (similar to the same treatment materials/agents that can be delivered through the infusion lumen) can be delivered through the catheter and exit out to the distal end of the catheter. Thus, the treatment material/agent may be delivered to the treatment area between the balloons (the treatment material/agent being delivered at an angle to the axial length of the catheter) and/or out through the end of the catheter (along the axial length of the catheter) during the same procedure.

Figure 15A:
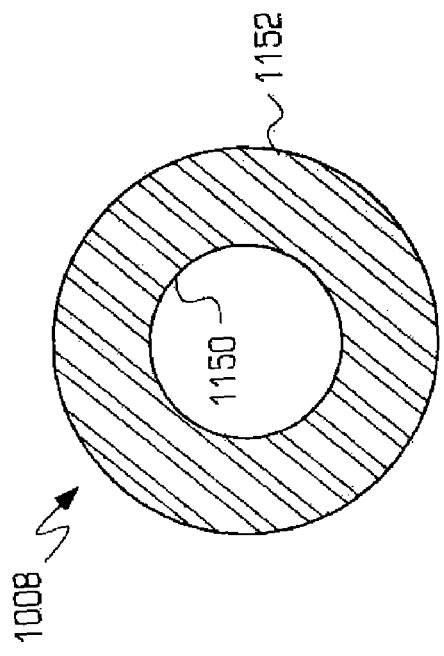
FIGS. 15A and 15B illustrates more details of a guidewire extension that is part of the multi-function catheter shown in FIG. 11.
Figure 15B:
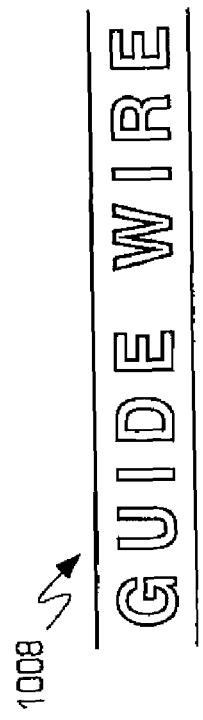

FIGS. 15A and 15B illustrates more details of a guidewire extension 1008 that is part of the multi-function catheter shown in FIG. 11. The guidewire extension may include a legend on the outside indicating that it is the guidewire extension as shown in FIG. 15B. In this embodiment, the guidewire extension may have an inner diameter 1150 of 0.039 mm and an outer diameter 1152 of 0.079 mm.

FIGS. 16A and 16B illustrates more details of an infusion extension 1006 that is part of the multi-function catheter shown in FIG. 11. The infusion extension may include a legend on the outside indicating that it is the infusion extension as shown in FIG. 16B. In this embodiment, the infusion extension may have an inner diameter 1160 of 0.025 mm and an outer diameter 1152 of 0.079 mm.

FIGS. 17A and 17B illustrates more details of a balloon extension 1110 that is part of the multi-function catheter shown in FIG. 11. The inflation extension may include a legend on the outside indicating that it is the inflation extension as shown in FIG. 17B. In this embodiment, the inflation extension may have an inner diameter 1170 of 0.025 mm and an outer diameter 1152 of 0.079 mm.

FIGS. 18-21 illustrate more details of the treatment portion 1121 of the multi-function catheter shown in FIG. 11. The treatment portion has the locations bands 936 placed as shown as well as the proximal and distal balloons 922, 924 shown in the un-inflated state and a treatment region 1180 located between the balloons. In one embodiment, the treatment portion 1121 may have an overall length, a, of 37 mm, a length from the first balloon to the tip 938, b, of 31 mm, a length, c, from the second balloon to the tip of 12 mm and a length d of the tip portion 938 of 5 mm. The treatment region 1180 may, in one embodiment, be a length, e, of 5 mm and each balloon may have a length, f, of 7 mm. As shown in more detail in FIGS. 19-21, a bypass inlet portion 1190 before the proximal balloon 942 may have one or more holes 1194 with the spacing between the holes shown in FIG. 20 (in millimeters) that allow fluid, such as blood, to flow through the tip and out of the holes 1194 (and bypass the treatment site) so that the catheter does not block the normal flow in the artery or vein as the treatment is being performed. The treatment region 1180 between the balloons also has one or more holes 1196 on one or both sides of the catheter with the spacing between the holes shown in FIG. 21 (in millimeters) that allow the treatment material/agent provided through the infusion lumen to be applied to the treatment area wherein the balloons, when inflated, keep the treatment material/agent localized to the treatment site as described above.

The multi-function catheter shown in FIG. 11 (and the subsequent figures) may be used for various treatments. For example, the multi-function catheter may be used for solid tumor treatment in which a physician may push particular fluids into the tumor bed using the catheter or infuse a solution more viscous than blood into the tumor bed to embolize the tumor (described below in more detail). The multi-function catheter may also be used to deliver embolic particles out of the distal tip (with a 300 um maximum size for the example catheter described above). The multi-function catheter may also be used for the treatments of arteriovenous malformations (ACMs). The multi-function catheter may also be used for gene therapy or general endovascular use.

FIGS. 22A and 22B illustrates more details of a distal tip portion 938 of the multi-function catheter shown in FIG. 11. As described above, the tip is radiopaque and may further have a passageway 1200 as shown in FIG. 22B that allows the normal fluid flow in the artery or vein being treated to continue to flow and bypass the treatment site so that the normal fluid flow does not dilute the treatment being performed. The passageway 1200 may also allow a treatment material to be delivered to the distal end of the catheter as described above.

In addition to the treatments described above, the various embodiments of the multi-function catheter may be used to embolize a tumor. In particular, the treatment material may be a mixture that is more viscous than blood so that, once the treatment material is infused into the tumor using the multi-function catheter, blood cannot displace the treatment material so that the tumor loses some or all of its blood supply and shrinks or dies. In one embodiment, the treatment material may be a mixture of saline and contrast agent (approximately 50%) or a chemotherapy agent and a contrast agent.

Having described one or more embodiments of the multi-function catheter and use thereof (which are intended to be illustrative and not limiting), it is noted that modifications and variations can be made by persons skilled in the art in light of the above teachings. For example, although the embodiments depicted herein show two balloon elements in a balloon assembly, the balloon assembly is not so limited. Therefore, it is understood that changes may be made in the particular embodiments disclosed which are within the scope and spirit of what is described as defined by the appended claims.

The invention claimed is:

1. A method of delivering a treatment material to a treatment area, the method comprising:
providing a catheter with a distally tapered body that is attached to spaced-apart balloons, the tapered body comprising a distal face and tapered sidewall with a diameter between 1.17 mm and 0.76 mm, the catheter having a first lumen for delivering inflation material to the spaced-apart balloons, a second lumen configured to directly deliver treatment material between the spaced-apart balloons a third lumen for holding a guide wire, the third lumen comprising a bypass opening in a sidewall of the third lumen for allowing biological fluid to pass simultaneously into and out of the third lumen while the spaced apart balloons are inflated, each lumen extending along the catheter, and wherein the first lumen is larger than the second lumen and the third lumen, and wherein the third lumen has a generally constant size along the distally tapered body of the catheter;
positioning the catheter with the aid of a guide wire located within the third lumen so that the area of treatment is between the spaced-apart balloons;
simultaneously controlling an inflation level of the spaced-apart balloons to create the treatment area between the spaced-apart balloons, wherein the controlling includes passing an inflation material through the first lumen that has an opening into each of the spaced-apart balloons;
withdrawing the guide wire to allow fluid to pass through the third lumen while the spaced-apart balloons are inflated; and
passing the treatment material through a second lumen into the treatment area.

2. The method of claim 1 further comprising inflating the spaced-apart balloons until the spaced-apart balloons touch the treatment area and form an isolated area between the spaced-apart balloons.

3. The method of claim 2 further comprising allowing a biological fluid to flow through a third lumen to allow a biological fluid to flow through the catheter and around the area between the spaced-apart balloons when the spaced-apart balloons are inflated.

4. The method of claim 1 further comprising positioning the spaced-apart balloons by using a marker that is located at predetermined positions relative to the spaced-apart balloons.

5. The method of claim 1, wherein the treatment material comprises a chemotherapy agent.

6. The method of claim 1, wherein the treatment material comprises an imaging agent.

7. The method of claim 1, wherein the treatment material is an embolic material.

8. The method of claim 1, wherein the treatment material further comprises a viscous treatment material that embolizes a tumor.

9. The method of claim 8, wherein the viscous treatment material further comprises a mixture of a contrast agent and a second material.

10. The method of claim 9, wherein the second material further comprises one of a chemotherapy agent and a saline agent.

11. The method of claim 1 further comprising perfusing a treatment material through an open distal end of the catheter.

12. A method of isolating an area of treatment, the method comprising:
providing a catheter with a distally tapered body that is attached to spaced-apart proximal and distal balloons, the tapered body comprising a distal face and a tapered sidewall with a diameter between 1.17 mm and 0.76 mm, the catheter having a treatment lumen extending along the catheter for directly delivering treatment material to a treatment chamber bounded by the proximal and distal balloon elements and a biological path wall upon inflation, a bypass lumen for holding a guide wire, wherein the bypass lumen comprises a bypass opening proximal to the proximal balloon to allow biological fluid to pass simultaneously into and out of the bypass lumen, wherein the bypass lumen has a generally constant size along the distally tapered body of the catheter;
positioning the catheter with the aid of a guide wire so that the area of treatment is between the spaced-apart balloons; and
simultaneously controlling an inflation level of the spaced-apart balloons by passing a first inflation material through an inflation lumen that has an opening into each of the spaced-apart balloons to isolate the area of treatment, and wherein the inflation lumen is larger than the treatment lumen and the bypass lumen;
withdrawing the guide wire from the catheter while the spaced-apart balloons are inflated to allow fluid to pass through the area of treatment.

13. The method of claim 12 further comprising adding an imaging agent to the area of treatment and inflating the balloons until there is no leakage of the imaging agent to areas around the area of treatment.

* * * * *